United States Patent
Kaji et al.

(10) Patent No.: US 10,961,185 B2
(45) Date of Patent: Mar. 30, 2021

(54) STABILIZER AND STABILIZATION METHOD

(71) Applicant: FUJIFILM WAKO PURE CHEMICAL CORPORATION, Osaka (JP)

(72) Inventors: Shinya Kaji, Amagasaki (JP);
Toshinari Ohashi, Amagasaki (JP);
Naoyuki Yamamoto, Amagasaki (JP)

(73) Assignee: FUJIFILM WAKO PURE CHEMICAL CHEMICAL CORPORATION, Osaka (JP)

( * ) Notice: Subject to any disclaimer, the term of this patent is extended or adjusted under 35 U.S.C. 154(b) by 155 days.

(21) Appl. No.: 15/770,145

(22) PCT Filed: Oct. 20, 2016

(86) PCT No.: PCT/JP2016/081083
§ 371 (c)(1),
(2) Date: Apr. 20, 2018

(87) PCT Pub. No.: WO2017/069192
PCT Pub. Date: Apr. 27, 2017

(65) Prior Publication Data
US 2018/0290969 A1   Oct. 11, 2018

(30) Foreign Application Priority Data
Oct. 21, 2015 (JP) .............................. JP2015-207370

(51) Int. Cl.
| | | |
|---|---|---|
| C09K 11/07 | (2006.01) | |
| C07C 309/50 | (2006.01) | |
| C07C 245/08 | (2006.01) | |
| C07C 245/10 | (2006.01) | |
| G01N 21/76 | (2006.01) | |
| C07C 309/46 | (2006.01) | |
| C09K 15/28 | (2006.01) | |
| G01N 33/50 | (2006.01) | |
| C07C 309/35 | (2006.01) | |
| C07C 309/43 | (2006.01) | |
| C07C 309/42 | (2006.01) | |
| C07C 309/47 | (2006.01) | |
| C09K 11/02 | (2006.01) | |

(52) U.S. Cl.
CPC .......... *C07C 309/50* (2013.01); *C07C 245/08* (2013.01); *C07C 245/10* (2013.01); *C07C 309/35* (2013.01); *C07C 309/42* (2013.01); *C07C 309/43* (2013.01); *C07C 309/46* (2013.01); *C07C 309/47* (2013.01); *C09K 11/07* (2013.01); *C09K 15/28* (2013.01); *G01N 21/76* (2013.01); *G01N 33/50* (2013.01); *C09K 11/02* (2013.01); *C09K 2211/1018* (2013.01)

(58) Field of Classification Search
CPC ............ G01N 21/76; C09K 2211/1018; C07C 309/35; C07C 309/42; C07C 309/43; C07C 309/46; C07C 309/47; C07C 309/50; C07C 245/08; C07C 245/10
See application file for complete search history.

(56) References Cited

U.S. PATENT DOCUMENTS

| | | | | |
|---|---|---|---|---|
| 2010/0078589 | A1* | 4/2010 | Iiyama | ................... B01D 15/00 |
| | | | | 252/79.5 |
| 2017/0038377 | A1* | 2/2017 | Merandon | ........ G01N 33/54393 |

FOREIGN PATENT DOCUMENTS

| | | |
|---|---|---|
| IN | 1429/KOL2010 A | 2/2012 |
| JP | H04-316049 A | 11/1992 |
| JP | H05-072729 A | 3/1993 |
| WO | WO 2015/155248 A1 | 10/2015 |

OTHER PUBLICATIONS

National Diagnostics. Product Guide for the Diogenes Cellular Luminescence Enhancement System for Superoxide Detection. 1998. (Year: 1998).*
Diaz, A. N. et al., "Chemical indicators as enhancers of the chemiluminescent luminol-H2O2-horseradish peroxidase reaction". J. Photochem. Photobiol. A: Chem. 1995, 87(2), 99-103. (Year: 1995).*

(Continued)

*Primary Examiner* — Richard A Huhn
(74) *Attorney, Agent, or Firm* — Leydig, Voit & Mayer, Ltd.

(57) ABSTRACT

The invention relates to a stabilizer for L-012 or a salt thereof, a stabilization method for L-012 or a salt thereof, coexisting with the stabilizer and L-012 or a salt thereof, and the like. The stabilizer is represented by Formula [1]:

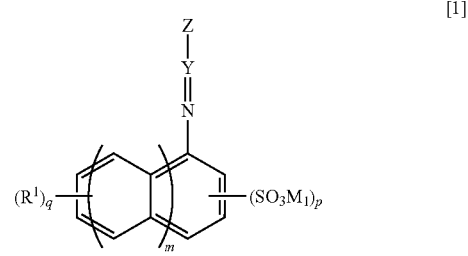

wherein p pieces of M1 each independently represent a hydrogen atom or an alkali metal atom, q pieces of R1 each independently represent a hydroxy group or a sulfonic acid group, m represents 0 or 1, p represents an integer of 1 to 3, q represents an integer of 0 to 4, Y represents a nitrogen atom or a CH group (a methine group), and Z represents an aryl group having a specific structure or a pyrazolyl group having a specific structure.

18 Claims, No Drawings

(56) References Cited

OTHER PUBLICATIONS

II et al., "Improved Enzyme Immunoassay for Human Basic Fibroblast Growth Factor Using a New Enhanced Chemiluminescence System," *Biochem. Biophys. Res. Commun.*, 193(2): 540-545 (1993).
Imada et al., *Seikaq*, 69(7): 728, Abstract 3423 (1997).
Nishinaka et al., "A New Sensitive Chemiluminescence Probe, L-012, for Measuring the Production of Superoxide Anion by Cells," *Biochem. Biophys. Res. Commun.*, 193(2): 554-559 (1993).
Japanese Patent Office, International Search Report in International Patent Application No. PCT/JP2016/081083 (dated Jan. 10, 2017).
Daiber et al., "Measurement of NAD(P)H Oxidase-Derived Superoxide with the Luminol Analogue L-012," *Free Radical Biol. Med.*, 36(1): 101-111 (2004).
Sheremet'ev et al., "Reactions of the Synthesis of Azo Dyes in Solidified Gelatin Gel and Their Analytical Application in the Determination of Nitrites," *J. Anal. Chem.*, 62(4): 319-324 (2007).
European Patent Office, Extended European Search Report in European Patent Application No. 16857505.8 (dated Jun. 5, 2019).

\* cited by examiner

STABILIZER AND STABILIZATION METHOD

CROSS-REFERENCE TO RELATED APPLICATIONS

This patent application is the U.S. national phase of International Patent Application No. PCT/JP2016/081083, filed Oct. 20, 2016, which claims the benefit of Japanese Patent Application No. 2015-207370, filed on Oct. 21, 2015, which are incorporated by reference in their entireties herein.

TECHNICAL FIELD

The present invention relates to a stabilizer, a stabilization method, a composition, and a kit for measuring a luminescence, of 8-amino-5-chloro-7-phenylpyrido[3,4-d]pyridazine-1,4(2H,3H)-dione (hereinafter sometimes simply referred to as L-012) or a salt thereof.

BACKGROUND ART

Analytical methods using chemiluminescent reactions have been actively studied as a measurement system in an immunological field since they can allow measurements with high sensitivity. In enzyme immunoassay methods in which antigens or antibodies are labeled with enzymes, chemiluminescent reactions are utilized in the measurement of enzyme activities, and luminol or a luminol derivative such as isoluminol is used as a chemiluminescent material. In the quantification of materials that exist only in trace amounts in vivo, it is necessary to detect a target material with high sensitivity, and therefore, luminol or a luminol derivative has been widely used as a compound having an excellent chemiluminescent quantum yield.

Meanwhile, L-012 (or a salt thereof) is known to have a luminescence intensity which is higher by 10 times or more than that of luminol (for example, Non-Patent Literature 1), and there have been examples reporting quantification of a basic fibroblast growth factor (for example, Non-Patent Literature 2), detection/quantification of superoxide radicals (for example, Non-Patent Literature 3), and the like. Thus, L-012 (or a salt thereof) has attracted attention as an excellent chemiluminescent material which replaces luminol.

CITATION LIST

Non-Patent Literature

Non-Patent Literature 1: Imada, et al., Biochemistry Vol. 69, No. 7, 3423 (1997)
Non-Patent Literature 2: Biochem. Biophys. Res. Commun., Vol. 193, 540-545 (1993)
Non-Patent Literature 3: Biochem. Biophys. Res. Commun., Vol. 193, 554-559 (1993)

SUMMARY OF INVENTION

Technical Problem

However, L-012 or a salt thereof has a problem in that its measurement sensitivity decreases upon exposure to natural light (for example, sunlight) or artificial light (for example, light derived from a fluorescent lamp). As a result, exposure to the natural light or the artificial light in a process for producing a measurement reagent containing L-012 or a salt thereof or during the use of the measurement reagent with a measurement system using L-012 or a salt thereof can cause a decrease in measurement sensitivity, and thus lead to generation of errors in the values measured. In this regard, there has been a demand for development of a stabilizer for L-012 or a salt thereof, which does not give an adverse effect during measurements and can suppress a decrease in measurement sensitivity by exposure.

The present invention has been made in consideration of the circumstances, and aims to provide a stabilizer which does not give an adverse effect during measurements and can suppress a phenomenon that the measurement sensitivity of a measurement solution (a luminescent substrate solution) containing L-012 or a salt thereof decreases by exposure.

Solution to Problem

The present invention includes the following configurations.

(1) A stabilizer represented by the general formula [1] that stabilizes 8-amino-5-chloro-7-phenylpyrido[3,4-d]pyridazine-1,4(2H,3H)-dione (L-012) or a salt thereof (hereinafter sometimes simply referred to as the stabilizer of the present invention);

General Formula [1]

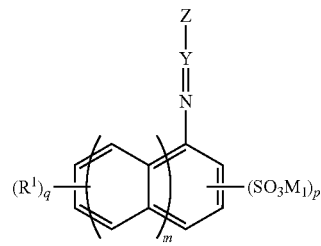

wherein, p pieces of $M_1$ each independently represent a hydrogen atom or an alkali metal atom, q pieces of $R^1$ each independently represent a hydroxy group or a sulfonic acid group represented by the general formula [A], m represents 0 or 1, p represents an integer of 1 to 3, q represents an integer of 0 to 4, Y represents a nitrogen atom or a CH group (a methine group), and Z represents a group represented by the general formula [Z-1], a group represented by the general formula [Z-2], or a group represented by the general formula [Z-3], General Formula [A]

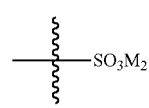

wherein, $M_2$ represents a hydrogen atom or an alkali metal atom,

General Formula [Z-1]

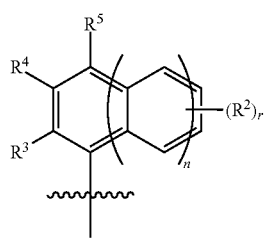

wherein, r pieces of $R^2$ each independently represent a hydroxy group or the sulfonic acid group represented by the general formula [A], $R^3$ represents a hydrogen atom or a hydroxy group, $R^4$ represents a hydrogen atom or the sulfonic acid group represented by the general formula [A], $R^5$ represents a hydrogen atom, a phenylamino group represented by the formula [B], or a naphthylazo group represented by the general formula [C], n represents 0 or 1, and r represents an integer of 0 to 4, Formula [B]

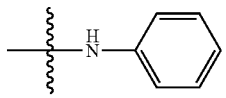

[B]

General Formula [C]

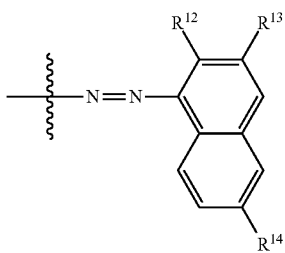

[C]

wherein, $R^{12}$ to $R^{14}$ each independently represent a hydrogen atom, a hydroxy group, or the sulfonic acid group represented by the general formula [A], General Formula [Z-2]

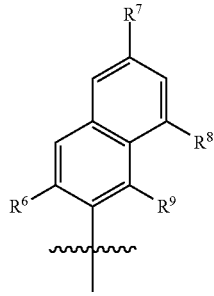

[Z-2]

wherein, $R^6$ to $R^9$ each independently represent a hydrogen atom, a hydroxy group, or the sulfonic acid group represented by the general formula [A], General Formula [Z-3]

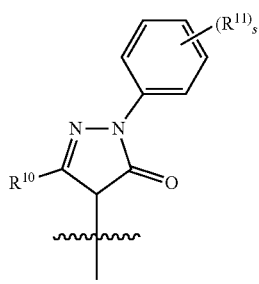

[Z-3]

wherein, $R^{10}$ represents a hydrogen atom or a carboxylic acid group represented by the general formula [D], s pieces of $R^{11}$ each independently represent a hydroxy group or the sulfonic acid group represented by the general formula [A], and s represents an integer of 0 to 5, General Formula [D]

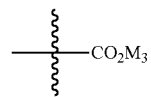

[D]

wherein, $M_3$ represents a hydrogen atom or an alkali metal atom.

(2) A stabilization method for 8-amino-5-chloro-7-phenylpyrido[3,4-d]pyridazine-1,4(2H,3H)-dione (L-012) or a salt thereof, wherein a compound represented by the general formula [1] is coexisted with 8-amino-5-chloro-7-phenylpyrido[3,4-d]pyridazine-1,4(2H,3H)-dione (L-012) or a salt thereof (hereinafter sometimes simply referred to as the stabilization method of the present invention);

General Formula [1]

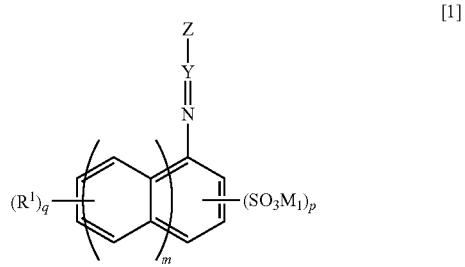

[1]

wherein, p pieces of $M_1$ each independently represent a hydrogen atom or an alkali metal atom, q pieces of $R^1$ each independently represent a hydroxy group or a sulfonic acid group represented by the general formula [A], m represents 0 or 1, p represents an integer of 1 to 3, q represents an integer of 0 to 4, Y represents a nitrogen atom or a CH group (a methine group), and Z represents a group represented by the general formula [Z-1], a group represented by the general formula [Z-2], or a group represented by the general formula [Z-3], General Formula [A]

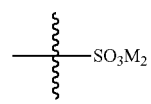

[A]

wherein, $M_2$ represents a hydrogen atom or an alkali metal atom,

General Formula [Z-1]

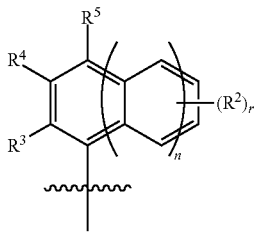

[Z-1]

wherein, r pieces of $R^2$ each independently represent a hydroxy group or the sulfonic acid group represented by the general formula [A], $R^3$ represents a hydrogen atom or a hydroxy group, $R^4$ represents a hydrogen atom or the sulfonic acid group represented by the general formula [A], $R^5$ represents a hydrogen atom, a phenylamino group represented by the formula [B], or a naphthylazo group represented by the general formula [C], n represents 0 or 1, and r represents an integer of 0 to 4, Formula [B]

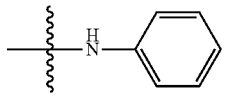

General Formula [C]

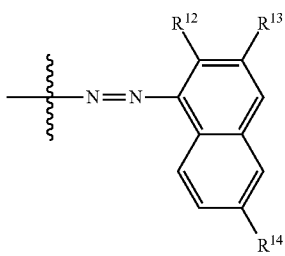

wherein, $R^{12}$ to $R^{14}$ each independently represent a hydrogen atom, a hydroxy group, or the sulfonic acid group represented by the general formula [A], General Formula [Z-2]

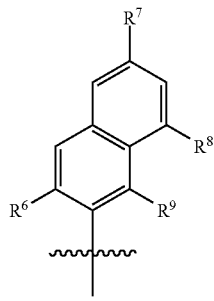

wherein, $R^6$ to $R^9$ each independently represent a hydrogen atom, a hydroxy group, or the sulfonic acid group represented by the general formula [A], General Formula [Z-3]

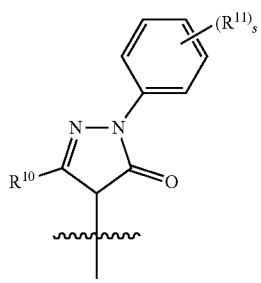

wherein, $R^{10}$ represents a hydrogen atom or a carboxylic acid group represented by the general formula [D], s pieces of $R^{11}$ each independently represent a hydroxy group or the sulfonic acid group represented by the general formula [A], and s represents an integer of 0 to 5, General Formula [D]

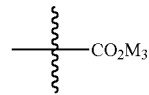

wherein, $M_3$ represents a hydrogen atom or an alkali metal atom.

(3) A composition comprising 8-amino-5-chloro-7-phenylpyrido[3,4-d]pyridazine-1,4(2H,3H)-dione (L-012) or a salt thereof, and the compound represented by the general formula [1] (hereinafter sometimes simply referred to as the composition of the present invention).

(4) A kit for measuring a luminescence, comprising 8-amino-5-chloro-7-phenylpyrido[3,4-d]pyridazine-1,4(2H,3H)-dione (L-012) or a salt thereof, and the compound represented by the general formula [1] (hereinafter sometimes simply referred to as the kit for measuring a luminescence of the present invention).

Advantageous Effects of Invention

The stabilizer of the present invention is a compound with a specific structure having an azo group or an imino group, and a benzenesulfonic acid group, and can suppress a reduction in the luminescence intensity (a decrease in the measurement sensitivity) of L-012 or a salt thereof, caused by decomposition (deterioration) with light, or the like while maintaining a luminescence dose that L-012 or a salt thereof itself has, by coexisting with the stabilizer of the present invention and L-012 or a salt thereof.

In addition, the composition of the present invention and the kit for measuring a luminescence of the present invention contain L-012 or a salt thereof, and the compound represented by the general formula [1] (the stabilizer of the present invention), and a reduction in the luminescence intensity (a decrease in the measurement sensitivity) of L-012 or a salt thereof due to exposure is suppressed in the process of producing the composition or the kit or during the use (measurement) of the composition or the kit. Therefore, in a case where the composition or the kit is used, target materials can be measured with high sensitivity and high accuracy.

DESCRIPTION OF EMBODIMENTS

In the present invention, 8-amino-5-chloro-7-phenylpyrido[3,4-d]pyridazine-1,4(2H,3H)-dione (L-012) or a salt thereof is a compound represented by the formula [X-1] or a salt thereof;

Formula [X-1]

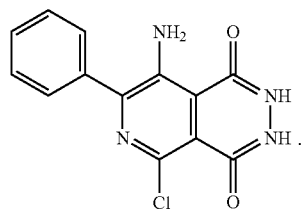

The salt of the compound represented by the formula [X-1] means a compound in which a carbonyl group of a pyridopyridazine ring in the compound is enolated to form a salt together with a monovalent or divalent cation. Examples of such a monovalent cation include alkali metal ions such as for example, a sodium ion, a potassium ion, and a lithium ion; for example, ammonium ion; monoalkylammonium ions having 1 to 4 carbon atoms, such as for example, a methylammonium ion, an ethylammonium ion, a propylammonium ion, and a butylammonium ion; dialkylammonium ions having 2 to 8 carbon atoms, such as for example, a dimethylammonium ion, a diethylammonium ion, a dipropylammonium ion, and a dibutylammonium ion; trialkylammonium ions having 3 to 12 carbon atoms, such as for example, a trimethylammonium ion, a triethylammonium ion, a tripropylammonium ion, and a tributylammonium ion; tetraalkylammonium ions having 4 to 16 carbon atoms, such as for example, a tetramethylammonium ion, a tetraethylammonium ion, a tetrapropylammonium ion, and a tetrabutylammonium ion; and other ammonium ions such as a pyridinium ion and a hydrazinium ion. Examples of such a divalent cation include alkaline earth metal ions such as for example, a magnesium ion and a calcium ion. Among these monovalent or divalent cations, a sodium ion is preferable.

Specific examples of the salt of the compound represented by the formula [X-1] include 8-amino-5-chloro-7-phenylpyrido[3,4-d]pyridazine-1,4(2H,3H)-dione, sodium salt, represented by the formula [X-2];

Formula [X-2]

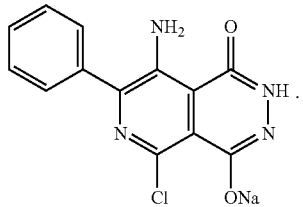

[X-2]

Among the 8-amino-5-chloro-7-phenylpyrido[3,4-d]pyridazine-1,4(2H,3H)-dione (L-012) or a salt thereof (the compound represented by the formula [X-1] or a salt thereof), 8-amino-5-chloro-7-phenylpyrido[3,4-d]pyridazine-1,4(2H,3H)-dione (L-012: the compound represented by the formula [X-1]) and 8-amino-5-chloro-7-phenylpyrido[3,4-d]pyridazine-1,4(2H,3H)-dione, sodium salt (the compound represented by the formula [X-2]) are preferable, and among these, 8-amino-5-chloro-7-phenylpyrido[3,4-d]pyridazine-1,4(2H,3H)-dione, sodium salt (the compound represented by the formula [X-2]) is more preferable. It should be noted that a commercially available product may be used or a product appropriately synthesized by a known method may also be used as L-012 or a salt thereof.

—Stabilizer of the Present Invention—

The stabilizer of the present invention is represented by the general formula [1];

General Formula [1]

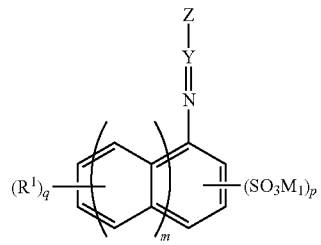

[1]

wherein, p pieces of $M_1$ each independently represent a hydrogen atom or an alkali metal atom, q pieces of $R^1$ each independently represent a hydroxy group or a sulfonic acid group represented by the general formula [A], m represents 0 or 1, p represents an integer of 1 to 3, q represents an integer of 0 to 4, Y represents a nitrogen atom or a CH group (a methine group), and Z represents a group represented by the general formula [Z-1], a group represented by the general formula [Z-2], or a group represented by the general formula [Z-3], General Formula [A]

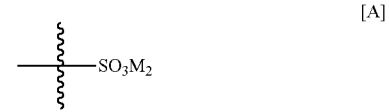

[A]

wherein, $M_2$ represents a hydrogen atom or an alkali metal atom,

General Formula [Z-1]

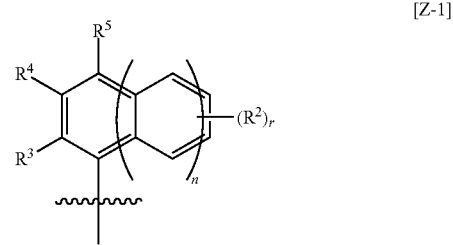

[Z-1]

wherein, r pieces of $R^2$ each independently represent a hydroxy group or the sulfonic acid group represented by the general formula [A], $R^3$ represents a hydrogen atom or a hydroxy group, $R^4$ represents a hydrogen atom or the sulfonic acid group represented by the general formula [A], $R^5$ represents a hydrogen atom, a phenylamino group represented by the formula [B], or a naphthylazo group represented by the general formula [C], n represents 0 or 1, and r represents an integer of 0 to 4, Formula [B]

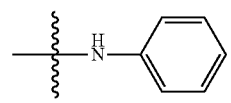

[B]

General Formula [C]

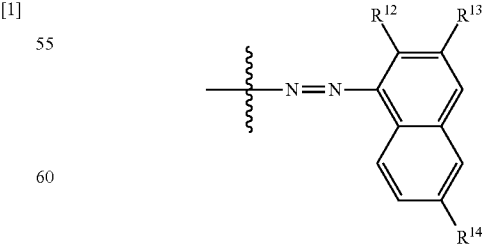

[C]

wherein, $R^{12}$ to $R^{14}$ each independently represent a hydrogen atom, a hydroxy group, or the sulfonic acid group represented by the general formula [A], General Formula [Z-2]

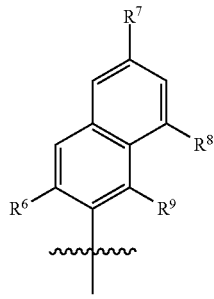

wherein, $R^6$ to $R^9$ each independently represent a hydrogen atom, a hydroxy group, or the sulfonic acid group represented by the general formula [A], General Formula [Z-3]

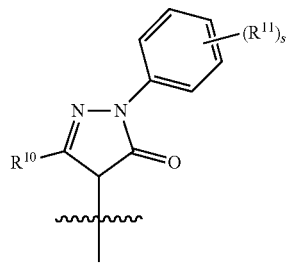

wherein, $R^{10}$ represents a hydrogen atom or a carboxylic acid group represented by the general formula [D], s pieces of $R^{11}$ each independently represent a hydroxy group or the sulfonic acid group represented by the general formula [A], and s represents an integer of 0 to 5, General Formula [D]

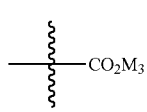

wherein, $M_3$ represents a hydrogen atom or an alkali metal atom.

The alkali metal atom represented by p pieces of $M_1$ in the general formula [1], $M_2$ in the general formula [A], and $M_3$ in the general formula [D] is preferably a lithium atom, a sodium atom, or a potassium atom and among these, more preferably the sodium atom.

In the general formula [1], Z is preferably a group represented by the general formula [Z-1].

As for r pieces of $R^2$ in the general formula [Z-1], all of $R^2$'s are preferably a sulfonic acid group represented by the general formula [A].

In the general formula [Z-1], $R^3$ is preferably a hydroxy group.

In the general formula [Z-1], $R^4$ is preferably a hydrogen atom.

In the general formula [Z-1], $R^5$ is preferably a hydrogen atom.

In the general formula [Z-2], $R^6$ and $R^7$ are preferably a sulfonic acid group represented by the general formula [A].

In the general formula [Z-2], $R^8$ and $R^9$ are preferably a hydroxy group.

In the general formula [Z-3], $R^{10}$ is preferably a carboxylic acid group represented by the general formula [D].

As for s pieces of $R^{11}$ in the general formula [Z-3], all of $R^{11}$'s are preferably a sulfonic acid group represented by the general formula [A].

In the general formula [C], $R^{12}$ is preferably a hydroxy group.

In the general formula [C], $R^{13}$ and $R^{14}$ are each preferably a sulfonic acid group represented by the general formula [A].

In the general formula [1], m is preferably 1.

In a case where m in the general formula [1] is 0, the ring represents a benzene ring, and in a case where m is 1, the ring represents a naphthalene ring. It should be noted that a case where m is 0 indicates that a group represented by q pieces of $R^1$ is not present.

In a case where n in the general formula [Z-1] is 0, the ring represents a benzene ring, in a case where n is 1, the ring represents a naphthalene ring. It should be noted that a case where n is 0 indicates that a group represented by r pieces of $R^2$ is not present.

In the general formula [1], p is preferably an integer of 1 or 2, and among these, more preferably 1.

In a case where the carbon atom to which a group represented by —N═Y—Z is bonded is a carbon atom at the position 1 of a benzene ring or a naphthalene ring, the sulfonic acid group represented by p pieces of —$SO_3M_1$ in the general formula [1] is preferably bonded to a carbon atom at the position 3 or 4 of the benzene ring or naphthalene ring.

In the general formula [1], q is preferably an integer of 0 to 2, and among these, more preferably 0 or 2. It should be noted that a case where q is 0 indicates that a group represented by $R^1$ is not present.

In a case where the carbon atom to which a group represented by —N═Y—Z is bonded is a carbon atom at the position 1 of a naphthalene ring, the group represented by q pieces of $R^1$ in the general formula [1] is preferably bonded to a carbon atom at the position 6 or 8 of the naphthalene ring.

In general formula [Z-1], r is preferably 2. It should be noted that a case where r is 0 indicates that a group represented by $R^2$ is not present.

In a case where the carbon atom to which a group represented by Y in the general formula [1] is bonded is a carbon atom at the position 1 of a naphthalene ring, the group represented by r pieces of $R^2$ in the general formula [Z-1] is preferably bonded to a carbon atom at the position 6 or 8 of the naphthalene ring.

In the general formula [Z-3], s is preferably an integer of 0 to 3, and among these, more preferably 1. It should be noted that a case where s is 0 indicates that a group represented by $R^{11}$ is not present.

In a case where the carbon atom to which a pyrazoline ring is bonded is a carbon atom at the position 1 of a benzene ring, the group represented by s pieces of $R^{11}$ in the general formula [Z-3] is preferably bonded to a carbon atom at the position 4 of the benzene ring.

The group represented by the general formula [Z-3] (the structure represented by the general formula [Z-3]) is sometimes isomerized to a group represented by the general formula [Z-4] (a structure represented by the general formula [Z-4]). In the present invention, even in a case where the stabilizer represented by the general formula [1] has a structure (enol type) represented by the general formula [Z-4], it is also encompassed by the stabilizer (represented by the general formula [1]) of the present invention;

General Formula [Z-4]
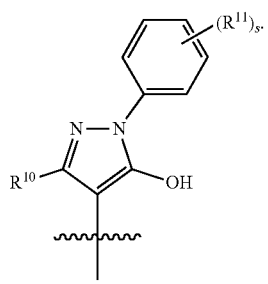
[Z-4]
Specific examples of the stabilizer of the present invention, represented by the general formula [1], include those represented by the formulae [1-1] to [1-6]. It should be noted that the stabilizer of the present invention is not limited to those represented by the formulae [1-1] to [1-6];
Formulae [1-1] to [1-6]
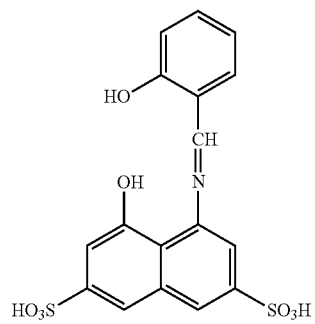
[1-1]
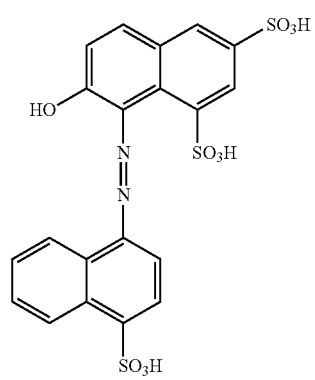
[1-2]
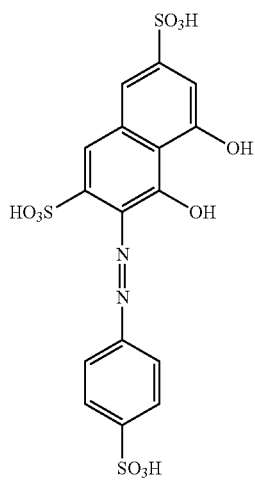
[1-3]
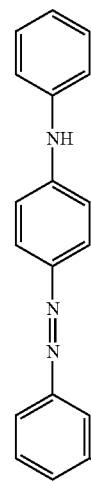
[1-4]
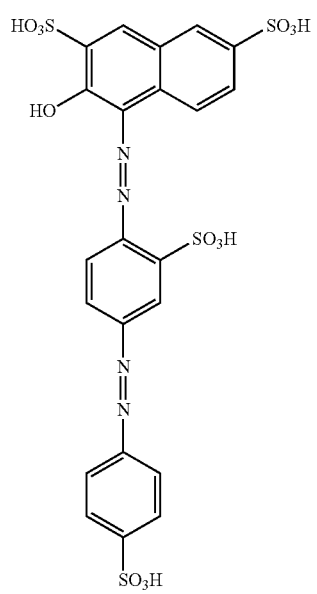
[1-5]

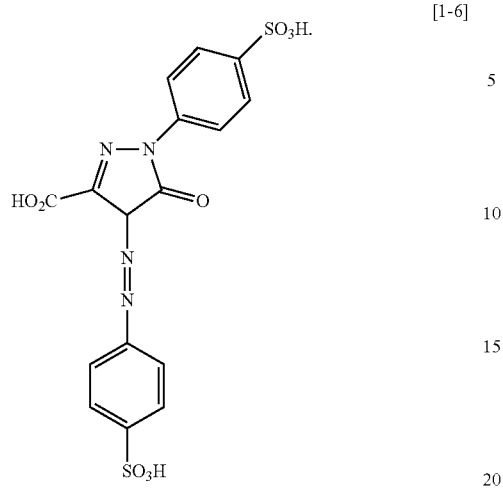

[1-6]

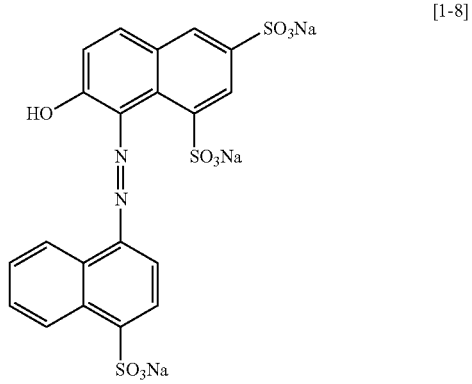

[1-8]

The names of the formulae [1-1] to [1-6] are as follows;

Formula [1-1]: 4-Hydroxy-5-(salicylidenamino)-2,7-naphthalenedisulfonic acid: Azomethine H, Formula [1-2]: 7-Hydroxy-8-(4-sulfo-1-naphthylazo)-1,3-naphthalenedisulfonic acid, Formula [1-3]: 2-(4-Sulfophenylazo)-1,8-dihydroxy-3,6-naphthalenedisulfonic acid, Formula [1-4]: 3-[4-(Phenylamino)phenylazo]benzenesulfonic acid, Formula [1-5]: 3-Hydroxy-4-[4-(4-sulfophenylazo)-2-sulfophenylazo]-2,7-naphthalenedisulfonic acid, Formula [1-6]: 4,5-Dihydro-5-oxo-1-(4-sulfophenyl)-4-[(4-sulfophenyl)azo]-1H-pyrazole-3-carboxylic acid.

In addition, the stabilizers represented by the formulae [1-1] to [1-6] may form salts together with alkali metals, and examples of the salts include those represented by the formulae [1-7] to [1-12]. It should be noted that the stabilizer of the present invention which is an alkali metal salt is not limited to those represented by the following formulae [1-7] to [1-12];

Formulae [1-7] to [1-12]

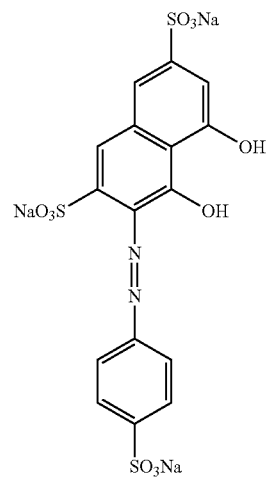

[1-9]

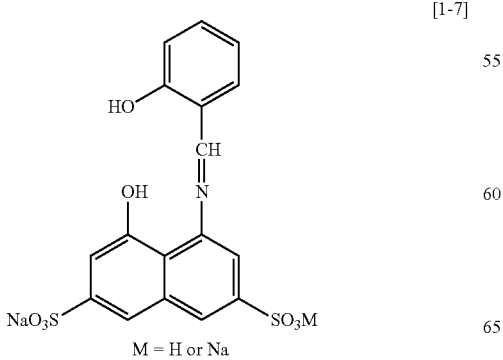

[1-7]

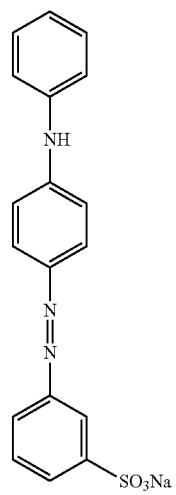

[1-10]

-continued

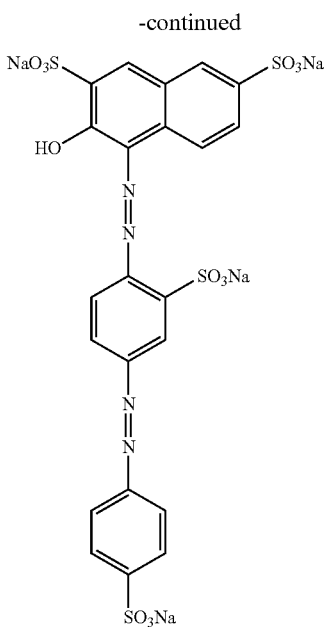

[1-11]

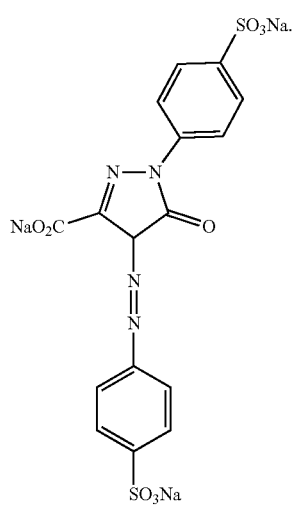

[1-12]

The names of the formulae [1-7] to [1-12] are as follows;

Formula [1-7]: 4-Hydroxy-5-(salicylidenamino)-2,7-naphthalenedisulfonic acid, sodium salt, or 4-hydroxy-5-(salicylidenamino)-2,7-naphthalenedisulfonic acid, disodium salt: Azomethine H, sodium salt, or Azomethine H, disodium salt, Formula [1-8]: 7-Hydroxy-8-(4-sulfo-1-naphthylazo)-1,3-naphthalenedisulfonic acid, trisodium salt: New Coccine, Formula [1-9]: 2-(4-Sulfophenylazo)-1,8-dihydroxy-3,6-naphthalenedisulfonic acid, trisodium salt: Sulfanilic acid azochromtrop, Formula [1-10]: 3-[4-(Phenylamino)phenylazo]benzenesulfonic acid, sodium salt: Metanil Yellow, Formula [1-11]: 3-Hydroxy-4-[4-(4-sulfophenylazo)-2-sulfophenylazo]-2,7-naphthalenedisulfonic acid, tetrasodium salt: Ponceau S, Formula [1-12]: 4,5-Dihydro-5-oxo-1-(4-sulfophenyl)-4-[(4-sulfophenyl)azo]-1H-pyrazole-3-carboxylic acid, trisodium salt: Tartrazine.

Since the stabilizer of the present invention has the specific structure represented by the general formula [1], it does not give an adverse effect during measurements and can suppress a decrease in measurement sensitivity due to exposure by coexisting with the stabilizer and L-012 or a salt thereof. The stabilizer of the present invention is also known as a common water-soluble dye. However, any of the water-soluble dyes do not necessarily have an effect of stabilizing L-012 or a salt thereof, and the effect of stabilizing L-012 or a salt thereof does not correlate with a maximum absorption wavelength of the dye. That is, the stabilizer of the present invention has an azo group or an imino group, and is characterized by its specific structure represented by the general formula [1], having a resonance structure. Thus, only the stabilizer of the present invention can have both of an effect of stabilizing L-012 or a salt thereof and an effect of not giving an adverse effect on measurements.

Among the stabilizers represented by the general formula [1], a stabilizer represented by the general formula [2] is preferable;

General Formula [2]

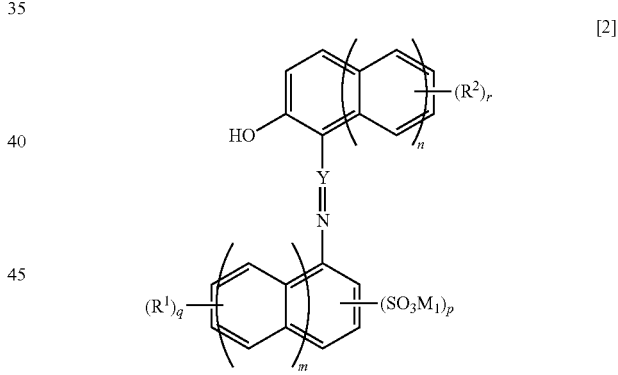

[2]

wherein, p pieces of $M_1$, q pieces of $R^1$, r pieces of $R^2$, m, n, p, q, r, and Y have the same definitions as above.

Specific examples of the stabilizers represented by the general formula [2] include those represented by the formulae [1-1], [1-2], [1-7], and [1-8].

Among the stabilizers of the present invention, the stabilizer represented by the general formula [2] does not give an adverse effect during measurements and exhibits an effect that a decrease in measurement sensitivity due to exposure can be effectively suppressed.

Moreover, among the stabilizers represented by the general formula [2], a stabilizer represented by the general formula [2'] is preferable;

General Formula [2']

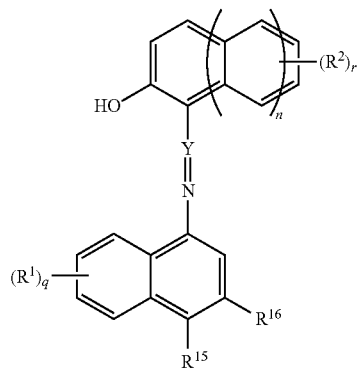

wherein, $R^{15}$ and $R^{16}$ each independently represent a hydrogen atom or a sulfonic acid group represented by the general formula [E], and q pieces of $R^1$, r pieces of $R^2$, n, q, r, and Y have the same definitions as above, provided that at least one of $R^{15}$ or $R^{16}$ is a sulfonic acid group represented by the general formula [E], General Formula [E]

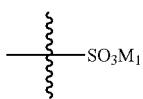

wherein, $M_1$ has the same definition as above.

Specific examples of the stabilizer represented by the general formula [2'] include those represented by the formulae [1-1], [1-2], [1-7], and [1-8].

A commercially available product may be used or a product appropriately synthesized by a known method may also be used as the stabilizer of the present invention.

—Stabilization Method of the Present Invention—

The stabilization method of the present invention is a method in which the compound represented by the general formula [1] (the stabilizer of the present invention) is coexisted with L-012 or a salt thereof.

A specific approach for the stabilization method of the present invention is not particularly limited as long as it is a method which can coexist with the compound represented by the general formula [1] (the stabilizer of the present invention) and L-012 or a salt thereof eventually, and examples thereof include (1) a method in which the compound represented by the general formula [1] (the stabilizer of the present invention) is added to a solution containing L-012 or a salt thereof to coexist with the compound represented by the general formula [1] (the stabilizer of the present invention) and L-012 or a salt thereof, (2) a method in which L-012 or a salt thereof is added to a solution containing the compound represented by the general formula [1](the stabilizer of the present invention) to coexist with the compound represented by the general formula [1] (the stabilizer of the present invention) and L-012 or a salt thereof, or (3) a method in which L-012 or a salt thereof, and the compound represented by the general formula [1] (the stabilizer of the present invention) are added to water or a dissolution solution such as a suitable buffer solution to coexist with the compound represented by the general formula [1] (the stabilizer of the present invention) and L-012 or a salt thereof.

In the stabilization method of the present invention, one kind of the compound (stabilizer) may be used singly, or two or more kinds of compounds (stabilizers) may be used in combination as the compound represented by the general formula [1] (the stabilizer of the present invention).

In the stabilization method of the present invention, the dissolution solution contained in L-012 or a salt thereof, and/or the compound represented by the general formula [1] (the stabilizer of the present invention) is not particularly limited as long as it is a solution used in the art, and specific examples thereof include water and a buffer solution.

The water for the stabilization method of the present invention is not particularly limited as long as it is water used in the art, and specific examples thereof include purified water such as distilled water and deionized water.

The buffer solution for the stabilization method of the present invention is not particularly limited as long as it is a buffer solution used in the art, and specific examples thereof include a (good) buffer solution obtained by dissolving a buffer such as N-(2-acetamido)-2-aminoethanesulfonic acid (ACES), N-(2-acetamide)iminodiacetic acid (ADA), N,N-bis(2-hydroxyethyl)-2-aminoethanesulfonic acid (BES), N, N-bis(2-hydroxyethyl)glycine (Bicine), bis(2-hydroxyethyl)iminotris(hydroxyethyl)methane (Bis-Tris), N-cyclohexyl-3-aminopropanesulfonic acid (CAPS), N-cyclohexyl-2-hydroxy-3-aminopropanesulfonic acid (CAPSO), N-cyclohexyl-2-aminoethanesulfonic acid (CHES), 3-[N,N-bis(2-hydroxyethyl)amino]-2-hydroxypropanesulfonic acid (DIPSO), 3-[4-(2-hydroxyethyl)-1-piperazinyl]propanesulfonic acid (EPPS), 2-[4-(2-hydroxyethyl)-1-piperazinyl]ethanesulfonic acid (HEPES), 2-hydroxy-3-[4-(2-hydroxyethyl)-1-piperazinyl]propanesulfonic acid (HEPPSO), 2-(N-morpholino)ethanesulfonic acid (MES), 3-(N-morpholino)propanesulfonic acid (MOPS), 2-hydroxy-3-(N-morpholino)propanesulfonic acid (MOPSO), piperazine-1,4-bis(2-ethanesulfonic acid) (PIPES), piperazine-1,4-bis(2-hydroxy-3-propanesulfonic acid) (POPSO), N-tris(hydroxymethyl)methyl-3-aminopropanesulfonic acid (TAPS), 2-hydroxy-N-tris(hydroxymethyl)methyl-3-aminopropanesulfonic acid (TAPSO), N-tris(hydroxymethyl)methyl-2-aminoethanesulfonic acid (TES), and N-[tris(hydroxymethyl)methyl]glycine (Tricine); a buffer solution obtained by dissolving a buffer such as phosphate, acetate, citrate, and tris(hydroxymethyl)aminomethane; a veronal buffer solution; and a borate buffer solution. In addition, as these buffer solutions, one kind of buffer solution may be used singly, two or more kinds of buffer solutions may be used in combination thereof, or buffer solutions formed by a combination of any of these buffer solutions with an alkali metal hydroxide such as sodium hydroxide and potassium hydroxide may be used. Specific examples of the combination of the buffer solutions include a 3-[4-(2-hydroxyethyl)-1-piperazinyl]propanesulfonic acid (EPPS)/sodium hydroxide buffer solution, a 2-hydroxy-3-[4-(2-hydroxyethyl)-1-piperazinyl]propanesulfonic acid (HEPPSO)/sodium hydroxide buffer solution, and a boric acid/sodium hydroxide buffer solution.

The concentration of the compound represented by the general formula [1](the stabilizer of the present invention) in the stabilization method of the present invention is not particularly limited as long as it is a concentration that makes it possible to stabilize L-012 or a salt thereof present in a reagent containing L-012 or a salt thereof or a solution such as a measurement solution (a luminescent substrate solution). As an example of the concentration to be used, the concentration varies by, for example, the type of the compound represented by the general formula [1](the stabilizer of the present invention), the concentration of L-012 or a salt thereof that coexists with the compound, the purity of the dissolution solution, or the like, but the concentration of the compound represented by the general formula [1] (the stabilizer of the present invention) in the solution in which L-012 or a salt thereof is present has a lower limit of usually 0.001 µM or more, preferably 0.01 µM or more, and more preferably 0.05 µM or more, and an upper limit of usually 1,000 µM or less, preferably 800 µM or less, and more preferably 500 µM or less.

The concentration of L-012 or a salt thereof in the stabilization method of the present invention may be appropriately selected from the concentration range used in the chemiluminescence measurement field, and specifically, the concentration of L-012 or a salt thereof in the solution has a lower limit of usually 0.01 mM or more, preferably 0.1 mM or more, and more preferably 0.3 mM or more, and an upper limit of usually 5 mM or less, preferably 2 mM or less, and more preferably 1 mM or less.

The concentration of the compound represented by the general formula [1](the stabilizer of the present invention) relative to the concentration of L-012 or a salt thereof {a concentration ratio of the compound represented by the general formula [1](the stabilizer of the present invention) to L-012 or a salt thereof} in the stabilization method of the present invention is not particularly limited as long as it is a concentration ratio that makes it possible to stabilize L-012 or a salt thereof. By way of an example of the concentration ratio, the concentration of the compound represented by the general formula [1] (the stabilizer of the present invention) in the solution with respect to the concentration of L-012 or a salt thereof in the solution of 1 mM has a lower limit of usually 0.002 µM or more, preferably 0.02 µM or more, and more preferably 0.1 µM or more, and an upper limit of usually 2,000 µM or less, preferably 1,600 µM or less, and more preferably 1,000 µM or less.

The concentration of the buffer in the buffer solution in the stabilization method of the present invention may be appropriately selected from a range of usually 10 to 500 mM, and preferably 10 to 300 mM.

The pH of the buffer solution in the stabilization method of the present invention may be appropriately selected from a range of usually pH 3 to 12, preferably pH 5 to 10, and more preferably pH 6.5 to 9.

In the stabilization method of the present invention, additives used in the art, for example, preservatives such as sodium azide; sugars such as maltose, sucrose, and trehalose; stabilizers such as protein; salts such as sodium chloride and magnesium chloride; antiseptics such as 5-chloro-2-methyl-4-isothiazolin-3-one, 2-methyl-4-isothiazolin-3-one, 5-bromo-5-nitro-1,3-dioxane, (+)-10-camphor sulfonic acid; and surfactants may coexist with the compound represented by the general formula [1] (the stabilizer of the present invention), L-012 or a salt thereof, and water and/or a buffer solution.

The amount of these additives to be added may be appropriately set within a range used in the art.

The stabilization method of the present invention which is carried out, based on the specific approach, is a method which stabilizes L-012 or a salt thereof for a long period of time by suppressing the decomposition (deterioration) of L-012 or a salt thereof due to exposure, and can suppress a reduction in the luminescence intensity (a decrease in the measurement sensitivity) of L-012 or a salt thereof. In addition, in a case where L-012 or a salt thereof is stabilized according to the stabilization method of the present invention, the compound represented by the general formula [1] (the stabilizer of the present invention) does not give an adverse effect on measurements during the use of a reagent or a measurement solution (a luminescent substrate solution) containing L-012 or a salt thereof, and therefore target materials can be measured with high sensitivity and high accuracy.

—Composition of the Present Invention—

The composition of the present invention contains L-012 or a salt thereof, and the compound represented by the general formula [1] (the stabilizer of the present invention), and suppresses a reduction in the luminescence intensity (a decrease in the measurement sensitivity) of L-012 or a salt thereof due to exposure, in a process of producing the composition and during the use (during the measurement) of the composition. For example, target materials in vivo can be measured with high sensitivity and high accuracy in a case where the composition of the present invention is used in the chemiluminescence measurement.

The composition of the present invention is generally in a solution state, but may also be in a frozen state or a lyophilized state.

The composition of the present invention contains L-012 or a salt thereof in the concentration range, and the compound represented by the general formula [1](the stabilizer of the present invention) in the concentration range at the concentration ratio.

For example, in a case where the composition of the present invention is in a solution state, L-012 or a salt thereof, and the compound represented by the general formula [1] (the stabilizer of the present invention) may be contained in a suitable dissolution solution such that they each satisfy the concentration range and the concentration ratio. In addition, in a case where the composition of the present invention is in a frozen state or a lyophilized state, L-012 or a salt thereof, and the compound represented by the general formula [1] (the stabilizer of the present invention) may be contained in a frozen stock solution or a lyophilized stock solution such that the concentration at a time of production of a dissolution solution satisfies the concentration range and the concentration ratio. It should be noted that in a case where the composition is produced using a dissolution solution, it is needless to say that L-012 or a salt thereof in the composition after the production can also be stabilized by making L-012 or a salt thereof in the concentration range and the compound represented by the general formula [1] (the stabilizer of the present invention) in the concentration range satisfy the concentration ratio.

Examples of the dissolution solution used in the composition of the present invention include the same ones as the specific examples of the water and buffer solution used in the stabilization method of the present invention, and the concentration or pH to be used is the same as the range.

In the composition of the present invention, additives used in the art may also coexist with L-012 or a salt thereof, the compound represented by the general formula [1] (the stabilizer of the present invention), and the dissolution solution. Examples of such additives include the same ones as the specific examples of the additives in the stabilization method of the present invention, and the addition amount thereof may also be appropriately set within the range used in the art.

—Luminescence Measurement Method Using Measurement Solution (Luminescent Substrate Solution) Containing L-012 or Salt Thereof, and Compound Represented by General Formula [1] (Stabilizer of the Present Invention)—

The compound represented by the general formula [1] (the stabilizer of the present invention) can be used in any of luminescence measurement methods in which L-012 or a salt thereof is present in a reaction system.

Specific examples of such a luminescence measurement method include for example, a method for detecting and measuring a chemiluminescence generated by the reaction of an oxidizing agent such as hydrogen peroxide with L-012 or a salt thereof, and principles thereof include various methods known per se, such as a sandwich method, a competitive method, and a double antibody method.

Specific examples of the chemiluminescence measurement using a reaction of an oxidizing agent with L-012 or a salt thereof include a method in which a catalyst in a sample is reacted with an oxidizing agent and L-012 or a salt thereof to generate a chemiluminescence, and a method in which an oxidizing agent in a sample is reacted with a catalyst and L-012 or a salt thereof to generate a chemiluminescence. These reactions are usually carried out in a solution, and depending on targets to be measured, there are (1) a method in which a measurement solution (a luminescent substrate solution) containing L-012 or a salt thereof, and the compound represented by the general formula [1] (the stabilizer of the present invention), a solution containing an oxidizing agent, and a solution containing a catalyst in a sample are mixed in an appropriate order to perform a reaction, (2) a method in which a measurement solution (a luminescent substrate solution) containing L-012 or a salt thereof, and the compound represented by the general formula [1] (the stabilizer of the present invention), a solution containing an oxidizing agent in a sample, and a solution containing a catalyst are mixed in an appropriate order to perform a reaction, (3) a method in which a measurement solution (a luminescent substrate solution) containing L-012 or a salt thereof, and the compound represented by the general formula [1] (the stabilizer of the present invention), a solution containing a oxidizing agent, a solution containing a catalyst, and a solution containing a sample are mixed in an appropriate order to perform a reaction, and the like. It should be noted that target materials may be directly involved in a main reaction or may be indirectly involved in a main reaction in the chemiluminescence measurement.

Examples of the catalyst include transition metal complexes containing iron ions such as potassium ferricyanide, copper ions, cobalt ions, or the like; enzymes such as a peroxidase (POD) and a catalase; and bio-components such as hemoglobin; and among these, the enzymes such as the peroxidase (POD) and the catalase are preferable, and the peroxidase (POD) is more preferable.

The peroxidase (POD) is not particularly limited as long as it can subject L-012 or a salt thereof to chemiluminescence in the presence of an oxidizing agent such as hydrogen peroxide. Specific examples of the peroxidase (POD) include those derived from plants such as horseradish, pineapple, and fig, those derived from microorganisms such as fungi and yeasts, and those derived from leukocytes and thyroid glands of animals, and among these, those derived from horseradish are preferable. It should be noted that such a peroxidase (POD) encompasses those produced by genetic engineering and those obtained by hydrolyzing a part of a structure of a naturally occurring peroxidase (POD) by a proteolytic enzyme or the like, and having a POD activity. In addition, the peroxidase (POD) may be as it is (unmodified) or may be chemically modified by, for example, an antigen, an antibody, or the like.

Examples of the oxidizing agent include hydrogen peroxide, sodium peroxide, sodium perchlorate, potassium perchlorate, sodium permanganate, potassium permanganate, and iodine, and among these, hydrogen peroxide is preferable. It should be noted that a commercially available product may be used as these oxidizing agents.

In the chemiluminescence measurement, a sensitizer (enhancer) may be used, in addition to L-012 or a salt thereof, the compound represented by the general formula [1] (the stabilizer of the present invention), the catalyst, and the oxidizing agent.

The sensitizer (enhancer) is not particularly limited as long as it is a sensitizer (enhancer) used in the art, and specific examples thereof include thiazole derivatives such as 4-(4-hydroxyphenyl)thiazole; imidazole derivatives such as 4-(imidazol-1-yl)phenol; oxazole derivatives such as 4-(4-hydroxyphenyl)oxazole; phenol derivatives such as p-iodophenol, 4-hydroxycinnamic acid, and 4-(4'-thiazolyl) phenol; and naphthol derivatives such as 1-bromonaphthol; and among these, the thiazole derivatives such as 4-(4-hydroxyphenyl)thiazole are preferable. It should be noted that one kind of sensitizer (enhancer) may be used singly, or two or more kinds of sensitizers (enhancers) may be used in combination as these sensitizers (enhancers). It should be noted that commercially available products may be used as the sensitizers (enhancers).

The amount of L-012 or a salt thereof to be used in the chemiluminescence measurement cannot be routinely said since it may vary depending on the modes of measurement in some cases. For example, in a case of measuring a total luminescence dose, the amount is usually 5 µL to 1 mL at a concentration of 0.01 to 5 mM, preferably 10 to 500 µL at a concentration of 0.1 to 2 mM, and more preferably 20 to 300 µL at a concentration of 0.3 to 1 mM, with respect to 25 µL of a sample. On the other hand, in a case of measuring the luminescence dose per unit time, the amount of L-012 or a salt thereof used is usually 5 µL to 1 mL at a concentration of 0.01 to 5 mM, preferably 10 to 500 µL at a concentration of 0.1 to 2 mM, and more preferably 20 to 300 µL at a concentration of 0.3 to 1 mM, with respect to 25 µL of a sample.

The amount of the compound represented by the general formula [1] (the stabilizer of the present invention) to be used in the chemiluminescence measurement cannot be routinely said since it may vary depending on the modes of measurement in some cases. For example, in a case of measuring a total luminescence dose, the amount is usually 5 µL to 1 mL at a concentration of 0.001 to 1,000 µM, preferably 10 to 500 µL at a concentration of 0.01 to 800 µM, and more preferably 20 to 300 µL at a concentration of 0.05 to 500 µM, with respect to 25 µL of a sample. On the other hand, in a case of measuring the luminescence dose per unit time, the amount of the compound represented by the general formula [1] (the stabilizer of the present invention) used is usually 5 µL to 1 mL at a concentration of 0.001 to 1,000 µM, preferably 10 to 500 µL at a concentration of 0.01 to 800 µM, and more preferably 20 to 300 µL at a concentration of 0.05 to 500 µM, with respect to 25 µL of a sample.

The concentration of the compound represented by the general formula [1](the stabilizer of the present invention) with respect to the concentration of L-012 or a salt thereof in the measurement solution (the luminescent substrate solution) containing L-012 or a salt thereof, and the compound represented by the general formula [1] (the stabilizer of the present invention) {a concentration ratio of the compound represented by the general formula [1] (the stabilizer of the present invention) to L-012 or a salt thereof} is the concentration of the compound represented by the general formula [1] (the stabilizer of the present invention) in the solution with respect to the concentration of L-012 or a salt thereof in the solution of 1 mM, and has a lower limit of usually 0.002 µM or more, preferably 0.02 µM or more, and more preferably 0.1 µM or more, and an upper limit of usually 2,000 µM or less, preferably 1,600 µM or less, and more preferably 1,000 µM or less.

The amount of the catalyst to be used in the chemiluminescence measurement cannot be routinely said since it may vary depending on the type of catalyst to be used or the modes of measurement in some cases. For example, in a case where the catalyst is a peroxidase (POD) and a total luminescence dose is measured, the amount is usually 5 µL to 1 mL at a concentration of 0.1 to 200 U/mL, preferably 10 to 500 µL at a concentration of 0.2 to 100 U/mL, and more preferably 20 to 300 µL at a concentration of 0.5 to 50 U/mL, with respect to 25 µL of a sample. On the other hand, in a case of measuring the luminescence dose per unit time, the amount of the peroxidase (POD) used is usually 5 µL to 1 mL at a concentration of 0.1 to 200 U/mL, preferably 10 to 500 µL at a concentration of 0.2 to 100 U/mL, and more preferably 20 to 300 µL at a concentration of 0.5 to 50 U/mL, with respect to 25 µL of a sample.

The amount of the oxidizing agent to be used in the chemiluminescence measurement cannot be routinely said since it may vary depending on the type of the oxidizing agent used and the modes of measurement in some cases. For example, in a case where the oxidizing agent is hydrogen peroxide and a total luminescence dose is measured, the amount is usually 5 µL to 1 mL at a concentration of 0.3 µM to 0.1 mM, preferably 10 to 500 µL at a concentration of 0.5 to 500 µM, and more preferably 20 to 300 µL at a concentration of 0.7 to 200 µM, with respect to 25 µL of a sample. On the other hand, in a case of measuring the luminescence dose per unit time, the amount of hydrogen peroxide used is usually 2.5 to 500 µL at a concentration of 0.3 µM to 0.1 mM, preferably 5 to 250 µL at a concentration of 0.5 to 500 µM, and more preferably 10 to 150 µL at a concentration of 0.7 to 200 µM, with respect to 25 µL of a sample.

The amount of the sensitizer (enhancer) to be used in the chemiluminescence measurement cannot be routinely said since it may vary depending on the type of the sensitizer (enhancer) used and the modes of measurement in some cases. For example, in a case where the sensitizer (enhancer) is a thiazole derivative and a total luminescence dose is measured, the amount is usually 5 µL to 1 mL at a concentration of 0.1 µM to 10 mM, preferably 10 to 500 µL at a concentration of 1 µM to 2 mM, and more preferably 20 to 300 µL at a concentration of 100 µM to 1 mM, with respect to 25 µL of a sample. On the other hand, in a case of measuring the luminescence dose per unit time, the amount of the thiazole derivative used is usually 5 µL to 1 mL at a concentration of 0.1 µM to 10 mM, preferably 10 to 500 µL at a concentration of 1 µM to 2 mM, and more preferably 20 to 300 µL at a concentration of 100 µM to 1 mM, with respect to 25 µL of a sample.

In the chemiluminescence measurement, additives used in the art, such as a surfactant and an activating agent, may be added to a measurement system for the purposes of avoiding the effects of components other than the target materials contained in a sample, enhancing the detection sensitivity of the target materials, or the like. In addition, the amounts of these additives to be added may be appropriately set within the range used in the art.

The luminescent reaction of L-012 or a salt thereof in the chemiluminescence measurement may be carried out under the condition of usually pH 3 to 12, preferably pH 5 to 10, and more preferably pH 6.5 to 9.

Adjustment of the pH to such a range may be carried out by adjusting the pH of a solution such as a measurement solution (a luminescent substrate solution), and the pH may be adjusted by, for example, using a buffer solution containing L-012 or a salt thereof, the compound represented by the general formula [1] (the stabilizer of the present invention), the catalyst, or the oxidizing agent. Examples of such a buffer solution include the same ones as the specific examples of the buffer solution mentioned for the stabilization method of the present invention, and the concentrations thereof to be used are also the same as the range.

The luminescent reaction of L-012 or a salt thereof in the chemiluminescence measurement, and the subsequent luminescence measurement may be carried out under the temperature condition of usually 10° C. to 60° C., preferably 15° C. to 50° C., and more preferably 20° C. to 45° C.

The time taken for the luminescent reaction of L-012 or a salt thereof in the chemiluminescence measurement, and the subsequent luminescence measurement is usually 10 seconds to 30 minutes, preferably 30 seconds to 20 minutes, and more preferably 30 seconds to 10 minutes.

In a case where an antigen-antibody reaction is performed using a labeled antigen or labeled antibody that is labeled with an enzyme such as a peroxidase (POD) as a catalyst to form an enzyme-labeled immune complex, and the complex is used in the chemiluminescence measurement, the antigen-antibody reaction may be carried out under the same conditions of the pH and the temperature as those of the luminescent reaction of L-012 or a salt thereof in the chemiluminescence measurement.

The reaction time for the antigen-antibody reaction is usually 10 seconds to 120 minutes, preferably 30 seconds to 60 minutes, and more preferably 1 to 30 minutes.

The compound represented by the general formula [1] (the stabilizer of the present invention) is suitably used in a method in which even during the chemiluminescence measurement, an antibody (labeled antibody) to a peroxidase (POD)-labeled specific component is reacted with a specific component to generate an immune complex of the specific component and the labeled antibody, and then the immune complex (to which POD is coupled), hydrogen peroxide, and L-012 or a salt thereof are reacted with each other to generate a chemiluminescence.

By way of an example, a method for measuring a hepatitis B virus surface antibody (hereinafter sometimes simply referred to as an HBs antibody) in a sample, using the compound represented by the general formula [1] (the stabilizer of the present invention), may be described, for example, as follows.

A sample, a solution containing a hepatitis B virus surface antigen (hereinafter sometimes simply referred to as an HBs antigen)-coupled magnetic particles, a peroxidase (POD)-labeled HBs antigen-containing solution, a solution (a luminescent substrate solution) containing L-012 or a salt thereof, the compound represented by the general formula [1] (the stabilizer of the present invention), and 4-(4-hydroxyphenyl)thiazole as a sensitizer (enhancer), and a hydrogen peroxide-containing solution are each loaded into an appropriate automatic analyzer provided with a mechanism for keeping a constant atmosphere in a reaction vessel and/or around the reaction vessel in a photometry chamber. Then, the machine is started, a sample containing the HBs antibody, and the solution containing the HBs antigen-coupled magnetic particles are reacted with each other to form an "HBs antigen-coupled magnetic particle-HBs antibody" complex, and B/F separation is performed. Subsequently, then, a POD-labeled HBs antigen-containing solution is added to and reacted with the solution containing the "HBs antigen-coupled magnetic particle-HBs antibody" complex to form an "HBs antigen-coupled magnetic particle-HBs antibody-POD-labeled HBs antigen" complex, and B/F separation is performed. Subsequently, the luminescent substrate solution and the hydrogen peroxide-containing solution are added to the magnetic particles subjected to the B/F separation, and mixed, and the luminescence of the sample may be measured.

As magnetic particles in the chemiluminescence measurement is not particularly limited as long as they are magnetic particles used in the art. A commercially available product may be used or a product appropriately synthesized by a known method may also be used as the magnetic particles. In addition, the preparation of antigen- or antibody-coupled magnetic particles, such as HBs antigen-coupled magnetic particles using the magnetic particles may be carried out in accordance with a method known per se.

In a case where chemiluminescence measurement is performed using a common spectrometer instead of an automatic analyzer, the luminescence of a sample may be measured by reacting a sample, various reagents, and the like by a manual method to perform a luminescent reaction, and then setting a reaction vessel in a spectrometer provided with a mechanism for keeping a constant atmosphere in a reaction vessel and/or around the reaction vessel in a photometry chamber.

The measurement system using the HBs antibody has been exemplified in the chemiluminescence measurement, but various target materials (subjects for measurement) can be measured with a use of the compound represented by the general formula [1] (the stabilizer of the present invention), and L-012 or a salt thereof. Such a target material (subject for measurement) is not particularly limited as long as an antibody or an antigen can be obtained therefrom by any methods, and examples thereof include all of the subjects for measurement which are considered measurable by ordinary complement immunoassay methods, such as drugs having biological and clinical importance, metabolites, vitamins, insecticides, steroids, peptides, hormones, hepatitis markers, cancer markers, antibodies, and serum proteins. By way of specific example, examples of endocrine function-related materials include thyroid-stimulating hormone (TSH), intact parathyroid hormone (iPTH), growth hormone (GH), somatomedin C (IGF-1), luteinizing hormone (LH), follicle-stimulating hormone (FSH), prolactin (PRL), adrenocorticotropic hormone (ACTH), vasopressin, oxytocin, somatostatin, enkephalin, β-endorphin, thyroxine, triiodothyronine, thyroglobulin, an anti-thyroglobulin antibody, an anti-T3 antibody, an anti-T4 antibody, an anti-TSH antibody, calcitonin, catecholamine, dopamine, serotonin, aldosterone, renin, angiotensin, cortisol, deoxycortisol, cortisone, corticosterone, deoxycorticosterone, androsterone, progesterone, pregnenolone, estrogen, estrone, estriol, estradiol, testosterone, gonadotropin, insulin, an anti-insulin antibody, C-peptide, glucagon, gastrin, secretin, cyclic AMP, cyclic GMP, prostaglandins, thromboxane, erythropoietin, and histamine; examples of tumor-related materials include CEA, ferritin, β2-microglobulin, elastase, α-fetoprotein, neuron-specific enolase, a prostatic specific antigen, and CA19-9; examples of drug- and vitamin-related materials include phenobarbital, phenytoin, carbamazepine, primidone, ethosuximide, valproic acid, acetazolamide, sulthiame, glutethimide, clonazepam, nitrazepam, diazepam, pentobarbital, secobarbital, bupivacaine, mepivacaine, lidocaine, procainamide, quinidine, digoxin, digitoxin, theophylline, amitriptyline, imipramine, amikacin, gentamicin, tobramycin, cefalexin, sulfamethoxazole, methotrexate, cyclosporin, methyl-prednisolone, salicylic acid, acetaminophen, indomethacin, allopurinol, vitamin A, carotene, vitamin B1, vitamin B2, vitamin B6, vitamin B12, folic acid, vitamin C, vitamin D, and vitamin E; examples of serum or plasma protein-related materials include albumin, α1-microglobulin, α1-antitrypsin, α2-macroglobulin, haptoglobulin, hemopexin, transferrin, myoglobin, IgG, IgM, IgA, IgD, IgE, fibrinogen, antithrombin, plasminogen, antiplasmin, protein C, a rheumatoid factor, an anti-DNA antibody, and C reactive protein; and examples of virus- and infectious disease-related materials include an HBs antigen, an HBs antibody, an HBc antibody, an HTLV-I antibody, an HTLV-III antibody, TPHA, various virus antigens, and various virus antibodies. Among these target materials (subjects for measurement), thyroid stimulating hormone (TSH), intact parathyroid hormone (iPTH), aldosterone, renin, cortisol, an HBs antibody, and an HBc antibody are preferable.

The concentrations of these target materials (subjects for measurement) in the chemiluminescence measurement may be appropriately selected from a concentration range in the art according to the types of the target materials (subjects for measurement).

As described above, in the chemiluminescence measurement using L-012 or a salt thereof, even though a measurement solution (a luminescent substrate solution) containing L-012 or a salt thereof is exposed by coexisting with the compound represented by the general formula [1] (the stabilizer of the present invention) and L-012 or a salt thereof, a reduction in luminescence intensity (a decrease in measurement sensitivity) of L-012 or a salt thereof can be suppressed, and an adverse effect is hardly given on the luminescence dose of L-012 or a salt thereof, and therefore, an effect that an adverse effect is not given during measurements, and a target material (a subject for measurement) can be measured with high sensitivity and high accuracy is exhibited. In addition, since in a case where the stabilizer of the present invention is coexisted with L-012 or a salt thereof, it is not necessary to subject the measurement solution (the luminescent substrate solution) containing L-012 or a salt thereof to light shielding, an effect that measurements can be performed more simply is exhibited.

—Kit for Measuring Luminescence of the Present Invention—

The kit for measuring a luminescence of the present invention is used in a method using the chemiluminescence of L-012 or a salt thereof, and as clearly shown from the specific examples of the luminescence measurement method, the kit contains a catalyst used in a method for measuring the chemiluminescence of L-012 or a salt thereof, reagents known per se such as an oxidizing agent, L-012 or a salt thereof, and the compound represented by the general formula [1] (the stabilizer of the present invention).

Specific examples of the kit for measuring a luminescence of the present invention include for example, a kit containing L-012 or a salt thereof, the compound represented by the general formula [1] (the stabilizer of the present invention), and an oxidizing agent; a kit containing L-012 or a salt thereof, the compound represented by the general formula [1] (the stabilizer of the present invention), and a catalyst; and a kit containing L-012 or a salt thereof, the compound represented by the general formula [1] (the stabilizer of the present invention), an oxidizing agent, and a catalyst.

Examples of such a kit for measuring a luminescence of the present invention are set forth below.

A kit for measuring a luminescence, containing A) L-012 or a salt thereof, B) the compound represented by the general formula [1] (the stabilizer of the present invention), and C) hydrogen peroxide.

A kit for measuring a luminescence, containing A) L-012 or a salt thereof, B) the compound represented by the general formula [1] (the stabilizer of the present invention), and D) a peroxidase (POD).

A kit for measuring a luminescence, containing A) L-012 or a salt thereof, B) the compound represented by the general formula [1] (the stabilizer of the present invention), C) hydrogen peroxide, and D) a peroxidase (POD).

The contents of L-012 or a salt thereof, the compound represented by the general formula [1] (the stabilizer of the present invention), and the reagents contained in the kit for measuring a luminescence of the present invention may be set such that the final concentrations and concentration ratios of the respective components such as L-012 or a salt thereof, the compound represented by the general formula [1] (the stabilizer of the present invention), and reagents are within the ranges during the chemiluminescence measurement.

The kit for measuring a luminescence of the present invention may contain additives used in the art, such as a sensitizer (enhancer), an activating agent, a preservative, a stabilizer, an antiseptic, and a surfactant, in addition to the reagents. In addition, the contents of these additives may be appropriately set from the range used in the art.

Examples of the kit for measuring a luminescence of the present invention containing such an additive include the following kits.

A kit for measuring a luminescence, containing A) L-012 or a salt thereof, B) the compound represented by the general formula [1] (the stabilizer of the present invention), C) hydrogen peroxide, and E) a sensitizer (enhancer).

A kit for measuring a luminescence, containing A) L-012 or a salt thereof, B) the compound represented by the general formula [1] (the stabilizer of the present invention), C) hydrogen peroxide, and F) magnetic particles.

A kit for measuring a luminescence, containing A) L-012 or a salt thereof, B) the compound represented by the general formula [1] (the stabilizer of the present invention), C) hydrogen peroxide, E) a sensitizer (enhancer), and F) magnetic particles.

The composition form in the kit for measuring a luminescence of the present invention may be any of a solution state, a frozen state, or a lyophilized state.

EXAMPLES

Hereinafter, the present invention is described in detail with reference to Examples and Comparative Examples, but the present invention is not limited to these examples by any means.

—Preparation of Reagents in Chemiluminescence Measurement System Using Peroxidase (POD), and Measurement of Chemiluminescence—

Preparation of reagents, and measurement methods and evaluation methods for chemiluminescence using various stabilizers or water-soluble dyes in general approaches for chemiluminescence measurement using a peroxidase (POD) are set forth below.

Examples 1 to 15 and Comparative Examples 1 to 14

(1) Preparation of Reagents for Measuring Luminescence, Solutions 1

(a) Preparation of Reagent for Measuring Luminescence, Solution 1-A (Examples 1 to 15 and Comparative Examples 1 to 12)

Into a 100 mL volumetric flask were introduced 15.6 mg of 8-amino-5-chloro-7-phenylpyrido[3,4-d]pyridazine-1,4 (2H,3H)-dione, sodium salt (manufactured by Wako Pure Chemical Industries, Ltd.) and 3.5 mg of 4-(4-hydroxyphenyl)thiazole (manufactured by Wako Pure Chemical Industries, Ltd.). Subsequently, various stabilizers or water-soluble dyes shown in Table 1 were added thereto in such amounts that the final concentrations during the chemiluminescence measurement reached predetermined concentrations shown in Table 1. In addition, 20 mL of a 2-hydroxy-3-[4-(2-hydroxyethyl)-1-piperazinyl]propanesulfonic acid (HEPPSO)/sodium hydroxide buffer solution (250 mM, pH 8.55) was added thereto, then the volume of the solution was adjusted to 100 mL with distilled water, and the solution was uniformly mixed at 25° C. to prepare a reagent for measuring a luminescence, Solution 1-A, which was stored under refrigeration (2° C. to 10° C.) until use in the measurement. It should be noted that commercially available products shown below were used as the stabilizers and the water-soluble dyes shown in Table 1.

Azomethine H: manufactured by Wako Pure Chemical Industries, Ltd.
New Coccine: manufactured by Wako Pure Chemical Industries, Ltd.
Sulfanilic acid azochromtrop: manufactured by Wako Pure Chemical Industries, Ltd.
Metanil Yellow: manufactured by Wako Pure Chemical Industries, Ltd.
Ponceau S: manufactured by Wako Pure Chemical Industries, Ltd.
Tartrazine: manufactured by Wako Pure Chemical Industries, Ltd.
N-Benzoyl H acid, monopotassium, monosodium salt: manufactured by Wako Pure Chemical Industries, Ltd.
Alizarin Yellow GG: manufactured by Tokyo Chemical Industry Co., Ltd.
Cresol Red: manufactured by Wako Pure Chemical Industries, Ltd.

(b) Preparation of Reagent for Measuring Luminescence, Solution 1-B (Comparative Example 13)

Into a 100 mL volumetric flask were introduced 15.6 mg of 8-amino-5-chloro-7-phenylpyrido[3,4-d]pyridazine-1,4 (2H,3H)-dione, sodium salt (manufactured by Wako Pure Chemical Industries, Ltd.) and 3.5 mg of 4-(4-hydroxyphenyl)thiazole (manufactured by Wako Pure Chemical Industries, Ltd.). Subsequently, 20 mL of a 2-hydroxy-3-[4-(2-hydroxyethyl)-1-piperazinyl]propanesulfonic acid (HEPPSO)/sodium hydroxide buffer solution (250 mM, pH 8.55) was added thereto, then the volume of the solution was adjusted to 100 mL with distilled water, and the solution was uniformly mixed at 25° C. to prepare a reagent for measuring a luminescence, Solution 1-B, which was stored under refrigeration (2° C. to 10° C.) until use in the measurement.

(c) Preparation of Reagent for Measuring Luminescence, Solution 1-C (Comparative Example 14)

Into a 100 mL volumetric flask were introduced 40 mg of luminol, sodium salt (manufactured by Wako Pure Chemical Industries, Ltd.) and 3.5 mg of 4-(4-hydroxyphenyl)thiazole (manufactured by Wako Pure Chemical Industries, Ltd.). Subsequently, 20 mL of a boric acid/sodium hydroxide buffer solution (250 mM, pH 8.55) was added thereto, then the volume of the solution was adjusted to 100 mL with distilled water, and the solution was uniformly mixed at 25° C. to prepare a reagent for measuring a luminescence, Solution 1-C, which was stored under refrigeration (2° C. to 10° C.) until use in the measurement.

(2) Preparation of Peroxidase (POD) Buffer Solution

A horseradish-derived POD (manufactured by Roche Diagnostics K.K.) was diluted with a 50 mM 2-(N-morpholino)ethanesulfonic acid (MES) buffer solution (pH 6.8) for preparation such that the concentration reached 0.02 µg/mL to obtain a POD buffer solution, which was stored under refrigeration (2° C. to 10° C.) until use in the measurement.

(3) Preparation of Reagent for Measuring Luminescence, Solution 2

Into a 100 mL volumetric flask was introduced 67 µL of aqueous hydrogen peroxide (manufactured by Wako Pure Chemical Industries, Ltd., special grade reagent, concentration of 30% by weight). Subsequently, the volume of the solution was adjusted to 100 mL with distilled water, and the solution was uniformly mixed at 25° C. to prepare a reagent for measuring a luminescence, Solution 2, which was stored under refrigeration (2° C. to 10° C.) until use in the measurement.

(4) Measurement of Chemiluminescence

A luminescence dose (average value) was measured, based on the reagents for measuring a luminescence, Solutions 1, according to Examples 1 to 15 and Comparative Examples 1 to 14 by the measurement method shown below, using each of the obtained reagents, and the photostabilization effect of various stabilizers or water-soluble dyes, and the presence or absence of an effect on the luminescence intensity of (a sodium salt of) L-012 were evaluated.

First, 1 mL of each of the reagents for measuring a luminescence, Solutions 1 (Solution 1-A, Solution 1-B, and Solution 1-C) obtained in (1) was transferred to two 5 mL test tubes. One of the test tubes was exposed to light from a fluorescent lamp at 430 to 450 Lx for 30 minutes (a reagent for measuring a luminescence with exposure, Solution 1), and the other was light-shielded by covering the test tube with aluminum foil (a reagent for measuring a luminescence with light shielding, Solution 1).

Subsequently, 100 µL of each of the reagents for measuring a luminescence with exposure, Solutions 1 (Solution 1-A, Solution 1-B, and Solution 1-C) or the reagents for measuring a luminescence with light shielding, Solutions 1 (Solution 1-A, Solution 1-B, and Solution 1-C), and 100 µL of the reagent for measuring a luminescence, Solution 2, were simultaneously added to 50 µL of the POD buffer solution to perform a luminescent reaction at 37° C. for 43 seconds, and the reagents for measuring a luminescence, Solution 1 and Solution 2, were simultaneously added thereto. Then, an average luminescence dose for 43 to 45 seconds was measured by a luminometer (Lumat LB9507: manufactured by Berthold Japan Co., Ltd.).

(5) Results

"The photostabilization effect of the stabilizers or the water-soluble dyes" and "the relative sensitivity with respect to luminol" were calculated from the obtained results, as shown below, and the various stabilizers or water-soluble dyes were evaluated. The results are each shown in Table 1.

<Photostabilization Effect of Stabilizers or Water-Soluble Dyes>

Regarding each of the reagents for measuring a luminescence, Solutions 1, a ratio of the average luminescence dose (luminescence dose with exposure) in the reagents for measuring a luminescence with exposure, Solutions 1 to the average luminescence dose (luminescence dose with light shielding) in the reagents for measuring a luminescence with light shielding, Solutions 1 [luminescence dose with exposure/luminescence dose with light shielding×100%=luminescence dose ratio] was calculated. The photostabilization effects of various stabilizers or water-soluble dyes were evaluated, based on the luminescence dose ratios.

That is, a luminescence dose ratio which is closer to 100% indicates that the photostabilization effects of various stabilizers or water-soluble dyes on (a sodium salt of) L-012 are high, and in view that the luminescence dose ratio was 64% in a case of using the reagent for measuring a luminescence, Solution 1-B, to which a stabilizer or water-soluble dye had not been added, the stabilizer or water-soluble dye contained in the reagent for measuring a luminescence, Solution 1-A, exhibiting a luminescence dose ratio of 70% or more, was evaluated to be a stabilizer or water-soluble dye which has a high photostabilization effect and can suppress a decrease in the measurement sensitivity during the exposure.

<Relative Sensitivity with Respect to Luminol>

Regarding each of the reagents for measuring a luminescence, Solution 1-A and Solution 1-B, a ratio of the luminescence dose with light shielding (L-012 luminescence dose) in each of the reagents for measuring a luminescence. Solution 1-A or Solution 1-B with respect to the luminescence dose with light shielding (luminol luminescence dose) in the reagent for measuring a luminescence, Solution 1-C [L-012 luminescence dose/luminol luminescence dose× 100%=relative sensitivity] was calculated. The measurement sensitivity of various stabilizers or water-soluble dyes was evaluated, based on the relative sensitivity.

That is, the reagent for measuring a luminescence, Solution 1-A, which exhibited a higher L-012 luminescence dose than the luminol luminescence dose (127,400 cps) was evaluated to be a reagent (L-012 luminescent reagent) having high measurement sensitivity and making it possible to perform measurements with higher sensitivity than that for the luminescence measurement using the luminol luminescence. In other words, the stabilizer or water-soluble dye contained in the reagent for measuring a luminescence, Solution 1-A, which exhibited a relative sensitivity of 100% or more, was evaluated to be a stabilizer or water-soluble dye which does not give an adverse effect on the luminescence intensity of L-012 and makes it possible to perform measurements with high sensitivity.

TABLE 1

| Examples | Reagent | Stabilizer | Concentration | Luminescence dose with light shielding | Luminescence dose with exposure | Luminescence dose ratio (%) | Relative sensitivity (%) |
|---|---|---|---|---|---|---|---|
| Example 1 | Solution 1-A | Azomethine H | 0.05 μM | 420,013 | 324,755 | 77 | 330 |
| Example 2 | Solution 1-A | | 0.1 μM | 321,084 | 288,631 | 90 | 252 |
| Example 3 | Solution 1-A | New Coccine | 0.5 μM | 532,621 | 386,421 | 73 | 418 |
| Example 4 | Solution 1-A | | 1 μM | 483,858 | 386,496 | 80 | 380 |
| Example 5 | Solution 1-A | Sulfanilic acid azochromtrop | 100 μM | 150,897 | 142,073 | 94 | 118 |
| Example 5 | Solution 1-A | Metanil Yellow | 10 μM | 515,642 | 367,129 | 71 | 405 |
| Example 6 | Solution 1-A | | 100 μM | 384,111 | 338,649 | 88 | 302 |
| Example 7 | Solution 1-A | | 500 μM | 269,610 | 270,733 | 100 | 212 |
| Example 8 | Solution 1-A | Ponceau S | 1 μM | 563,124 | 451,037 | 80 | 442 |
| Example 9 | Solution 1-A | | 10 μM | 519,605 | 442,909 | 85 | 408 |
| Example 10 | Solution 1-A | | 100 μM | 393,523 | 373,339 | 95 | 309 |
| Example 11 | Solution 1-A | | 500 μM | 146,533 | 154,195 | 105 | 115 |
| Example 12 | Solution 1-A | Tartrazine | 10 μM | 527,402 | 380,031 | 72 | 414 |
| Example 13 | Solution 1-A | | 100 μM | 434,319 | 359,961 | 83 | 341 |
| Example 14 | Solution 1-A | | 500 μM | 232,027 | 219,169 | 94 | 182 |
| Comparative Example 1 | Solution 1-A | N-Benzoyl H acid, mono-K, mono-Na | 1 μM | 307,410 | 201,453 | 66 | 241 |
| Comparative Example 2 | Solution 1-A | | 10 μM | 62,504 | 47,669 | 76 | 49 |
| Comparative Example 3 | Solution 1-A | | 100 μM | 1,392 | 1,253 | 90 | 1 |
| Comparative Example 4 | Solution 1-A | | 500 μM | 150 | 134 | 89 | 0.1 |
| Comparative Example 5 | Solution 1-A | Alizarin Yellow GG | 1 μM | 556,240 | 373,129 | 67 | 437 |
| Comparative Example 6 | Solution 1-A | | 10 μM | 583,699 | 368,105 | 63 | 458 |
| Comparative Example 7 | Solution 1-A | | 100 μM | 587,034 | 388,202 | 66 | 461 |
| Comparative Example 8 | Solution 1-A | | 500 μM | 576,029 | 385,218 | 67 | 452 |
| Comparative Example 9 | Solution 1-A | Cresol Red | 1 μM | 581,165 | 393,330 | 68 | 456 |
| Comparative Example 10 | Solution 1-A | | 10 μM | 534,693 | 357,498 | 67 | 420 |
| Comparative Example 11 | Solution 1-A | | 100 μM | 266,468 | 180,857 | 68 | 209 |
| Comparative Example 12 | Solution 1-A | | 500 μM | 38,863 | 35,253 | 91 | 31 |
| Comparative Example 13 | Solution 1-B | — | — | 565,837 | 362,385 | 64 | 444 |
| Comparative Example 14 | Solution 1-C | — | — | 127,400 | 115,387 | 91 | — |

Azomethine H: 4-Hydroxy-5-(salicylidenamino)-2,7-naphthalenedisulfonic acid
New Coccine: 7-Hydroxy-8-(4-sulfo-1-naphthylazo)-1,3-naphthalenedisulfonic acid, trisodium salt
Sulfanilic acid azochromtrop: 2-(4-Sulfophenylazo)-1,8-dihydroxy-3,6-naphthalenedisulfonic acid, trisodium salt
Metanil Yellow: 3-[4-(Phenylamino)phenylazo]benzenesulfonic acid, sodium salt
Ponceau S: 3-Hydroxy-4-[4-(4-sulfophenylazo)-2-sulfophenylazo]-2,7-naphthalenedisulfonic acid, tetrasodium salt
Tartrazine: 4,5-Dihydro-5-oxo-1-(4-sulfophenyl)-4-[(4-sulfophenyl)azo]-1H-pyrazole-3-carboxylic acid, trisodium salt
N-Benzoyl H acid, mono-K, mono-Na: 4-Benzoylamino-5-hydroxy-2,7-naphthalenedisulfonic acid, monopotassium, monosodium salt
Alizarin Yellow GG: 4-Hydroxy-3'-nitroazobenzene-3-carboxylic acid, sodium salt
Cresol Red: 3,3-Bis(3-methyl-4-hydroxyphenyl)-3H-2,1-benzoxathiole-1,1-dioxide From the results in Table 1, it could be seen that only Azomethine H, New Coccine, Sulfanilic acid azochromtrop, Metanil Yellow, Ponceau S, and Tartrazine, each of which is the stabilizer of the present invention, have both of an effect of suppressing a decrease in measurement sensitivity due to exposure (photostabilization effect) and an effect of making it possible to perform measurements with high sensitivity with little influence on the luminescence intensity of (a sodium salt of) L-012.

—Preparation of Reagent in Measurement System of Active Renin Using Peroxidase (POD) and Measurement of Active Renin—

Preparation of reagents, and measurement methods and evaluation methods for active renin using various stabilizers or water-soluble dyes in a measurement system of active renin using a peroxidase (POD) are set forth below.

Examples 16 to 28 and Comparative Examples 15 to 28

(1) Preparation of Reagents for Measuring Luminescence, Solutions 1

(a) Preparation of Reagent for Measuring Luminescence, Solution 1-A (Examples 16 to 28 and Comparative Examples 15 to 26)

Into a 100 mL volumetric flask were introduced 15.6 mg of 8-amino-5-chloro-7-phenylpyrido[3,4-d]pyridazine-1,4(2H,3H)-dione, sodium salt (manufactured by Wako Pure Chemical Industries, Ltd.) and 3.5 mg of 4-(4-hydroxyphenyl)thiazole (manufactured by Wako Pure Chemical Industries, Ltd.). Subsequently, various stabilizers or water-soluble dyes shown in Table 2 were added thereto in such amounts that the final concentrations during the chemiluminescence measurement reached predetermined concentrations shown in Table 2. In addition, 20 mL of a 2-hydroxy-3-[4-(2-hydroxyethyl)-1-piperazinyl]propanesulfonic acid (HEPPSO)/sodium hydroxide buffer solution (250 mM, pH 8.55) was added thereto, then the volume of the solution was adjusted to 100 mL with distilled water, and the solution was uniformly mixed at 25° C. to prepare a reagent for measuring a luminescence, Solution 1-A, which was stored under refrigeration (2° C. to 10° C.) until use in the measurement.

(b) Preparation of Reagent for Measuring Luminescence, Solution 1-B (Comparative Example 27)

Into a 100 mL volumetric flask were introduced 15.6 mg of 8-amino-5-chloro-7-phenylpyrido[3,4-d]pyridazine-1,4 (2H,3H)-dione, sodium salt (manufactured by Wako Pure Chemical Industries, Ltd.) and 3.5 mg of 4-(4-hydroxyphenyl)thiazole (manufactured by Wako Pure Chemical Industries, Ltd.). Subsequently, 20 mL of a 2-hydroxy-3-[4-(2-hydroxyethyl)-1-piperazinyl]propanesulfonic acid (HEPPSO)/sodium hydroxide buffer solution (250 mM, pH 8.55) was added thereto, then the volume of the solution was adjusted to 100 mL with distilled water, and the solution was uniformly mixed at 25° C. to prepare a reagent for measuring a luminescence, Solution 1-B, which was stored under refrigeration (2° C. to 10° C.) until use in the measurement.

(c) Preparation of Reagent for Measuring Luminescence, Solution 1-C (Comparative Example 28)

Into a 100 mL volumetric flask were introduced 40 mg of luminol, sodium salt (manufactured by Wako Pure Chemical Industries, Ltd.) and 3.5 mg of 4-(4-hydroxyphenyl)thiazole (manufactured by Wako Pure Chemical Industries, Ltd.). Subsequently, 20 mL of a boric acid/sodium hydroxide buffer solution (250 mM, pH 8.55) was added thereto, then the volume of the solution was adjusted to 100 mL with distilled water, and the solution was uniformly mixed at 25° C. to prepare a reagent for measuring a luminescence, Solution 1-C, which was stored under refrigeration (2° C. to 10° C.) until use in the measurement.

(2) Preparation of Reagent Containing Magnetic Particles (Anti-Renin Monoclonal Antibody (Mouse)-Coupled Magnetic Particle Reagent)

Into a lidded polyethylene bottle having 50 mL of a 97%-by-weight ethanol solution containing 3-aminopropyltriethoxysilane were added 12.5 mL of magnetic particles (prepared in accordance with Production Example 1 described in WO 2012/173002) to perform a reaction at 25° C. for 1 hour. Then, the magnetic particles were collected by magnetism, using a neodymium magnet, and the liquid was aspirated and removed by an aspirator. Subsequently, 50 mL of a 10 mM acetate buffer solution (pH 5.1) was added thereto, the bottle was capped, and the polyethylene bottle was slowly inverted twice and stirred, and then the magnetic particles were collected by magnetism using a neodymium magnet. The liquid was aspirated and removed by an aspirator, and the magnetic particles were washed. This washing operation was repeated four times.

The magnetic particles after the washing were added into a lidded polyethylene bottle having 50 mL of a 0.5%-by-weight ethanol solution of succinic anhydride to perform a reaction at 25° C. for 2 hours. After the reaction, 50 mL of a 100 mM 2-(N-morpholino)ethanesulfonic acid (MES) buffer solution (pH 5.0) was added thereto, the bottle was capped, and the polyethylene bottle was slowly inverted twice and stirred, and then the magnetic particles were collected by magnetism using a neodymium magnet. The liquid was aspirated and removed by an aspirator, and the magnetic particles were washed. This washing operation was repeated four times.

In addition, the magnetic particles after the washing were added into a lidded polyethylene bottle having 50 mL of a 100 mM MES buffer solution (pH 5.0) containing an anti-renin monoclonal antibody (mouse) (manufactured by ITM Co., Ltd.) at a concentration of 200 μg/mL to perform a reaction at 110° C. for 15 to 25 hours. After the reaction, the magnetic particles were collected by magnetism, using a neodymium magnet, and washed with an MES buffer solution, and then a blocking solution {a 50 mM MES buffer solution (pH 5.5) containing 0.5% Block Ace (manufactured by Snow Brand Milk Products Co., Ltd.)} was added thereto, and the mixture was reacted at 11° C. for 15 hours to prepare anti-renin monoclonal antibody (mouse)-coupled magnetic particles. These were diluted with a 50 mM MES buffer solution (pH 5.5) to a concentration of 0.5 mg/mL in terms of an anti-renin monoclonal antibody-coupled magnetic particle concentration to prepare a reagent containing antibody-coupled magnetic particles (an anti-renin monoclonal antibody (mouse)-coupled magnetic particle reagent), which was stored under refrigeration (2° C. to 10° C.) until use in the measurement.

(3) Preparation of Buffer Solution for Immune Reaction

A 50 mM 3-(N-morpholino)propanesulfonic acid (MOPS) buffer solution (pH 7.0) was prepared to obtain a buffer solution for an immune reaction, which was stored under refrigeration (2° C. to 10° C.) until use in the measurement.

(4) Preparation of Enzyme-Labeled Reagent (Peroxidase (POD)-Labeled Anti-Renin Monoclonal Antibody (Mouse) Reagent)

A POD-labeled anti-renin monoclonal antibody (mouse) was prepared by the method described in literature (S. YOSHITAKE, M. IMAGAWA, E. ISHIKAWA, H. OGAWA; J Biochem (1982) Vol. 92, (5): 1413-1424), using an anti-renin monoclonal antibody (mouse) (manufactured by ITM Co., Ltd.) and a horseradish-derived POD (manufactured by Roche Diagnostics K.K.). This was diluted with a 50 mM MES buffer solution (pH 6.5) to a concentration of 1.0 mL/L in terms of a POD-labeled anti-renin monoclonal antibody concentration to prepare an enzyme-labeled reagent (POD-labeled anti-renin monoclonal antibody (mouse) reagent), which was stored under refrigeration (2° C. to 10° C.) until use in the measurement.

(5) Preparation of Reagent for Measuring Luminescence, Solution 2

Into a 100 mL volumetric flask was introduced 67 μL of aqueous hydrogen peroxide (manufactured by Wako Pure Chemical Industries, Ltd., special grade reagent, concentration of 30% by weight). Subsequently, the volume of the solution was adjusted to 100 mL with distilled water, and the solution was uniformly mixed at 25° C. to prepare a reagent for measuring a luminescence, Solution 2, which was stored under refrigeration (2° C. to 10° C.) until use in the measurement.

(6) Measurement of Chemiluminescence

A luminescence dose (average value) was measured, based on the reagents for measuring a luminescence, Solutions 1, according to Examples 16 to 28 and Comparative Examples 15 to 28 by the measurement method shown below, using each of the obtained reagents, and the photostabilization effect of various stabilizers or water-soluble dyes, and the presence or absence of an effect on the luminescence intensity of (a sodium salt of) L-012 were evaluated.

First, 1 mL of each of Solution 1-A and Solution 1-B among the reagents for measuring a luminescence, Solutions 1, obtained in (1) was transferred to two 5 mL test tubes. One of the test tubes was exposed to light from a fluorescent lamp at 430 to 450 Lx for 30 minutes (a reagent for measuring a luminescence with exposure, Solution 1), and the other was light-shielded by covering the test tube with aluminum foil (a reagent for measuring a luminescence with light shielding, Solution 1). 1 mL of Solution 1-C was transferred to one 5 mL test tube, and the test tube was covered with aluminum foil to perform light shielding (reagent for measuring a luminescence with light shielding, Solution 1).

Subsequently, 10 to 50 µg of a reagent containing antibody-coupled magnetic particles (anti-renin monoclonal antibody (mouse)-coupled magnetic particle reagent), 25 µL of a standard renin solution at a renin concentration of 25 pg/mL, prepared with a 15 mM phosphate buffer solution (pH 7.2) containing 1% bovine serum albumin, and 50 µL of a buffer solution for an immune reaction were added to and mixed in a test tube to perform a reaction at 37° C. for 3 minutes to form an "anti-renin monoclonal antibody (mouse)-coupled magnetic particle-renin" complex. After the reaction, the magnetic particles were collected by magnetism, using a neodymium magnet, the liquid was aspirated and removed by an aspirator, and then 100 µL of physiological saline was added thereto to disperse the magnetic particles, followed by collection by magnetism, and a washing operation for aspirating and removing the liquid by the aspirator was repeated three times.

Subsequently, 50 µL of the enzyme-labeled reagent (POD-labeled anti-renin monoclonal antibody (mouse) reagent) was added into the test tube to perform a reaction at 37° C. for 3 minutes to form an "anti-renin monoclonal antibody (mouse)-coupled magnetic particle-renin-POD-labeled anti-renin monoclonal antibody (mouse)" complex. After the reaction, the magnetic particles were collected by magnetism, using a neodymium magnet, the liquid was aspirated and removed by an aspirator, and then 100 µL of physiological saline was added thereto to disperse the magnetic particles, followed by collection by magnetism, and a washing operation for aspirating and removing the liquid by the aspirator was repeated twice.

Finally, 100 µL of each of the reagents for measuring a luminescence with exposure, Solutions 1 (Solution 1-A and Solution 1-B) or the reagents for measuring a luminescence with light shielding, Solutions 1 (Solution 1-A, Solution 1-B, and Solution 1-C), and 100 µL of the reagent for measuring a luminescence, Solution 2, were simultaneously added thereto to perform a luminescent reaction at 37° C. for 43 seconds. Then, an average luminescence dose for 43 to 45 seconds after adding the reagents for measuring a luminescence, Solutions 1 and Solution 2 simultaneously, was measured by a luminometer (Lumat LB9507: manufactured by Berthold Japan Co., Ltd.).

(7) Results

"The photostabilization effect of the stabilizers or the water-soluble dyes" and "the relative sensitivity with respect to luminol" were calculated from the obtained results, as shown below, and the various stabilizers or water-soluble dyes were evaluated. The results are each shown in Table 2.

<Photostabilization Effect of Stabilizers or Water-Soluble Dyes>

Regarding each of the reagents for measuring a luminescence, Solutions 1, a ratio of the average luminescence dose (luminescence dose with exposure) in the reagents for measuring a luminescence with exposure, Solutions 1 to the average luminescence dose (luminescence dose with light shielding) in the reagents for measuring a luminescence with light shielding, Solutions 1 [luminescence dose with exposure/luminescence dose with light shielding×100%=luminescence dose ratio] was calculated. The photostabilization effects of various stabilizers or water-soluble dyes were evaluated, based on the luminescence dose ratios.

That is, a luminescence dose ratio which is closer to 100% indicates that the photostabilization effects of various stabilizers or water-soluble dyes on (a sodium salt of) L-012 are high, and in view that the luminescence dose ratio was 75% in a case of using the reagent for measuring a luminescence, Solution 1-B, to which a stabilizer or water-soluble dye had not been added, the stabilizer or water-soluble dye contained in the reagent for measuring a luminescence, Solution 1-A, exhibiting a luminescence dose ratio of 80% or more, was evaluated to be a stabilizer or water-soluble dye which has a high photostabilization effect and can suppress a decrease in the measurement sensitivity during the exposure.

<Relative Sensitivity with Respect to Luminol>

Regarding each of the reagents for measuring a luminescence, Solution 1-A and Solution 1-B, a ratio of the luminescence dose with light shielding (L-012 luminescence dose) in each of the reagents for measuring a luminescence, Solution 1-A or Solution 1-B with respect to the luminescence dose with light shielding (luminol luminescence dose) in the reagent for measuring a luminescence, Solution 1-C [L-012 luminescence dose/luminol luminescence dose× 100%=relative sensitivity] was calculated. The measurement sensitivity of various stabilizers or water-soluble dyes was evaluated, based on the relative sensitivity.

That is, the reagent for measuring a luminescence, Solution 1-A, which exhibited a higher L-012 luminescence dose than the luminol luminescence dose (645,938 cps) was evaluated to be a reagent (L-012 luminescent reagent) having high measurement sensitivity and making it possible to perform measurements with higher sensitivity than that for the luminescence measurement using the luminol luminescence. In other words, the stabilizer or water-soluble dye contained in the reagent for measuring a luminescence, Solution 1-A, which exhibited a relative sensitivity of 100% or more, was evaluated to be a stabilizer or water-soluble dye which does not give an adverse effect on the luminescence intensity of L-012 and makes it possible to perform measurements with high sensitivity.

TABLE 2

| Examples | Reagent | Stabilizer | Concentration | Luminescence dose with light shielding | Luminescence dose with exposure | Luminescence dose ratio (%) | Relative sensitivity (%) |
|---|---|---|---|---|---|---|---|
| Example 15 | Solution 1-A | Azomethine H | 0.01 µM | 2,311,236 | 1,938,529 | 84 | 358 |
| Example 16 | Solution 1-A | | 0.05 µM | 2,024,893 | 1,687,683 | 83 | 313 |
| Example 17 | Solution 1-A | | 0.1 µM | 1,610,475 | 1,494,608 | 93 | 249 |
| Example 18 | Solution 1-A | New Coccine | 0.01 µM | 2,380,233 | 2,049,963 | 86 | 368 |
| Example 19 | Solution 1-A | | 0.05 µM | 2,157,873 | 1,904,557 | 88 | 334 |
| Example 20 | Solution 1-A | | 0.1 µM | 2,151,333 | 2,023,040 | 94 | 333 |
| Example 21 | Solution 1-A | | 0.5 µM | 2,197,549 | 2,099,667 | 96 | 340 |
| Example 22 | Solution 1-A | | 1 µM | 2,229,813 | 2,036,992 | 91 | 345 |
| Example 23 | Solution 1-A | | 5 µM | 2,214,335 | 2,060,100 | 93 | 343 |
| Example 24 | Solution 1-A | | 10 µM | 2,104,899 | 1,833,925 | 87 | 326 |
| Example 25 | Solution 1-A | | 50 µM | 1,853,872 | 1,674,785 | 90 | 287 |
| Example 26 | Solution 1-A | | 100 µM | 1,540,606 | 1,404,465 | 91 | 239 |
| Example 27 | Solution 1-A | Tartrazine | 500 µM | 836,626 | 671,949 | 80 | 130 |
| Comparative Example 15 | Solution 1-A | N-Benzoyl H acid, mono-K, mono-Na | 0.1 µM | 2,062,977 | 1,516,790 | 74 | 319 |
| Comparative Example 16 | Solution 1-A | | 1 µM | 1,197,130 | 909,074 | 76 | 185 |
| Comparative Example 17 | Solution 1-A | | 10 µM | 265,028 | 181,549 | 69 | 41 |
| Comparative Example 18 | Solution 1-A | | 500 µM | 352 | 311 | 88 | 0.05 |
| Comparative Example 19 | Solution 1-A | Alizarin Yellow GG | 0.1 µM | 2,035,000 | 1,542,823 | 76 | 315 |
| Comparative Example 20 | Solution 1-A | | 1 µM | 2,232,120 | 1,591,077 | 71 | 346 |
| Comparative Example 21 | Solution 1-A | | 10 µM | 2,231,313 | 1,632,327 | 73 | 345 |
| Comparative Example 22 | Solution 1-A | | 500 µM | 2,135,540 | 1,593,240 | 75 | 331 |
| Comparative Example 23 | Solution 1-A | Cresol Red | 0.1 µM | 2,148,887 | 1,683,293 | 78 | 333 |
| Comparative Example 24 | Solution 1-A | | 1 µM | 2,219,140 | 1,394,507 | 63 | 344 |
| Comparative Example 25 | Solution 1-A | | 10 µM | 2,022,827 | 1,468,023 | 73 | 313 |
| Comparative Example 26 | Solution 1-A | | 500 µM | 130,327 | 133,218 | 102 | 20 |
| Comparative Example 27 | Solution 1-B | — | — | 2,213,420 | 1,668,553 | 75 | 343 |
| Comparative Example 28 | Solution 1-C | — | — | 645,938 | — | — | — |

Azomethine H: 4-Hydroxy-5-(salicylidenamino)-2,7-naphthalenedisulfonic acid
New Coccine: 7-Hydroxy-8-(4-sulfo-1-naphthylazo)-1,3-naphthalenedisulfonic acid, trisodium salt
Tartrazine: 4,5-Dihydro-5-oxo-1-(4-sulfophenyl)-4-[(4-sulfophenyl)azo]-1H-pyrazole-3-carboxylic acid, trisodium salt
N-Benzoyl H acid, mono-K, mono-Na: 4-Benzoylamino-5-hydroxy-2,7-naphthalenedisulfonic acid, monopotassium, monosodium salt
Alizarin Yellow GG: 4-Hydroxy-3'-nitroazobenzene-3-carboxylic acid, sodium salt
Cresol Red: 3,3-Bis(3-methyl-4-hydroxyphenyl)-3H-2,1-benzoxathiole-1,1-dioxide From the results in Table 2, it could be seen that Azomethine H, New Coccine, and Tartrazine, each of which is the stabilizer of the present invention, have both of an effect of suppressing a decrease in measurement sensitivity due to exposure (photostabilization effect) and an effect of making it possible to perform measurements with high sensitivity with little influence on the luminescence intensity of (a sodium salt of) L-012.

—Preparation of Reagent in Measurement System of HBs Antibody Using Peroxidase (POD) and Measurement of HBs Antibody—

Preparation of reagents, and measurement methods and evaluation methods for HBs antibody using various stabilizers or water-soluble dyes in a measurement system of an HBs antibody using a peroxidase (POD) are set forth below.

Examples 29 to 44 and Comparative Examples 29 and 30

(1) Preparation of Reagents for Measuring Luminescence, Solutions 1

(a) Preparation of Reagent for Measuring Luminescence, Solution 1-A (Examples 29 to 44)

Into a 100 mL volumetric flask were introduced 15.6 mg of 8-amino-5-chloro-7-phenylpyrido[3,4-d]pyridazine-1,4 (2H,3H)-dione, sodium salt (manufactured by Wako Pure Chemical Industries, Ltd.) and 3.5 mg of 4-(4-hydroxyphenyl)thiazole (manufactured by Wako Pure Chemical Industries, Ltd.). Subsequently, various stabilizers or water-soluble dyes shown in Table 3 were added thereto in such amounts that the final concentrations during the chemiluminescence measurement reached predetermined concentrations shown in Table 3. In addition, 20 mL of a 2-hydroxy-3-[4-(2-hydroxyethyl)-1-piperazinyl]propanesulfonic acid (HEPPSO)/sodium hydroxide buffer solution (250 mM, pH 8.55) was added thereto, then the volume of the solution was adjusted to 100 mL with distilled water, and the solution was uniformly mixed at 25° C. to prepare a reagent for measuring a luminescence, Solution 1-A, which was stored under refrigeration (2° C. to 10° C.) until use in the measurement.

(b) Preparation of Reagent for Measuring Luminescence, Solution 1-B (Comparative Example 29)

Into a 100 mL volumetric flask were introduced 15.6 mg of 8-amino-5-chloro-7-phenylpyrido[3,4-d]pyridazine-1,4 (2H,3H)-dione, sodium salt (manufactured by Wako Pure Chemical Industries, Ltd.) and 3.5 mg of 4-(4-hydroxyphenyl)thiazole (manufactured by Wako Pure Chemical Industries, Ltd.). Subsequently, 20 mL of a 2-hydroxy-3-[4-(2-hydroxyethyl)-1-piperazinyl]propanesulfonic acid (HEPPSO)/sodium hydroxide buffer solution (250 mM, pH 8.55) was added thereto, then the volume of the solution was adjusted to 100 mL with distilled water, and the solution was uniformly mixed at 25° C. to prepare a reagent for measuring a luminescence, Solution 1-B, which was stored under refrigeration (2° C. to 10° C.) until use in the measurement.

(c) Preparation of Reagent for Measuring Luminescence, Solution 1-C (Comparative Example 30)

Into a 100 mL volumetric flask were introduced 40 mg of luminol, sodium salt (manufactured by Wako Pure Chemical Industries, Ltd.) and 3.5 mg of 4-(4-hydroxyphenyl)thiazole (manufactured by Wako Pure Chemical Industries, Ltd.). Subsequently, 20 mL of a boric acid/sodium hydroxide buffer solution (250 mM, pH 8.55) was added thereto, then the volume of the solution was adjusted to 100 mL with distilled water, and the solution was uniformly mixed at 25° C. to prepare a reagent for measuring a luminescence, Solution 1-C, which was stored under refrigeration (2° C. to 10° C.) until use in the measurement.

(2) Preparation of Reagent Containing Magnetic Particles (HBs Antigen-Coupled Magnetic Particle Reagent)

Into a lidded polyethylene bottle having 50 mL of a 97%-by-weight ethanol solution containing 3-aminopropyltriethoxysilane were added 12.5 mL of magnetic particles (prepared in accordance with Production Example 1 described in WO 2012/173002) to perform a reaction at 25° C. for 1 hour. Then, the magnetic particles were collected by magnetism, using a neodymium magnet, and the liquid was aspirated and removed by an aspirator. Subsequently, 50 mL of a 10 mM acetate buffer solution (pH 5.1) was added thereto, the bottle was capped, and the polyethylene bottle was slowly inverted twice and stirred, and then the magnetic particles were collected by magnetism using a neodymium magnet. The liquid was aspirated and removed by an aspirator, and the magnetic particles were washed. This washing operation was repeated four times.

The magnetic particles after the washing were added into a lidded polyethylene bottle having 1 mL of 25%-by-weight glutaraldehyde/9 mL of a sodium hydrogen carbonate buffer solution to perform a reaction at 25° C. for 1 hour. After the reaction, distilled water was added thereto, the bottle was capped, and the polyethylene bottle was slowly inverted twice and stirred, and then the magnetic particles were collected by magnetism using a neodymium magnet. The liquid was aspirated and removed by an aspirator, and the magnetic particles were washed. This washing operation was repeated three times.

In addition, the magnetic particles after the washing were added into a lidded polyethylene bottle having 8 mL of a 15 mM phosphate buffer solution (pH 7.2) containing an HBs antigen (manufactured by TRINA BIOREACTIVES AG) at a concentration of 2.24 mg/mL to perform a reaction at 25° C. for 2 hours. After the reaction, the magnetic particles were collected by magnetism, using a neodymium magnet, and washed with physiological saline, and then a blocking solution {a 50 mM MES buffer solution (pH 5.5) containing 0.5% Block Ace} was added thereto, and the mixture was reacted at 37° C. for 15 to 25 hours to prepare HBs antigen-coupled magnetic particles. These were diluted with a 50 mM 3-(N-morpholino)propanesulfonic acid (MOPS) buffer solution (pH 7.5) containing 0.5% of Block Ace (Manufactured by Snow Brand Milk Products Co., Ltd.) to a concentration of 0.5 mg/mL in terms of an HBs antigen-coupled magnetic particle concentration to prepare a reagent containing antigen-coupled magnetic particles (an HBs antigen-coupled magnetic particle reagent), which was stored under refrigeration (2° C. to 10° C.) until use in the measurement.

(3) Preparation of Enzyme-Labeled Reagent (Peroxidase (POD)-Labeled HBs Antigen Reagent)

A POD-labeled HBs antigen was prepared by the method described in literature (S. YOSHITAKE, M. IMAGAWA, E. ISHIKAWA, H. OGAWA; J Biochem (1982) Vol. 92, (5): 1413-1424), using an HBs antigen (manufactured by TRINA BIOREACTIVES AG) and a horseradish-derived POD (manufactured by Roche Diagnostics K.K.). This was diluted with a 50 mM MES buffer solution (pH 6.8) to a concentration of 1.0 mL/L in terms of a POD-labeled HBs antigen concentration to prepare an enzyme-labeled reagent (POD-labeled HBs antigen reagent), which was stored under refrigeration (2° C. to 10° C.) until use in the measurement.

(4) Preparation of Reagent for Measuring Luminescence, Solution 2

Into a 100 mL volumetric flask was introduced 67 µL of aqueous hydrogen peroxide (manufactured by Wako Pure Chemical Industries, Ltd., special grade reagent, concentration of 30% by weight). Subsequently, the volume of the solution was adjusted to 100 mL with distilled water, and the solution was uniformly mixed at 25° C. to prepare a reagent for measuring a luminescence, Solution 2, which was stored under refrigeration (2° C. to 10° C.) until use in the measurement.

(5) Measurement of Chemiluminescence

A luminescence dose (average value) was measured, based on the reagents for measuring a luminescence, Solutions 1, according to Examples to 29 to 44 and Comparative Examples 29 and 30 by the measurement method shown below, using each of the obtained reagents, and the photo-stabilization effect of various stabilizers or water-soluble dyes, and the presence or absence of an effect on the luminescence intensity of (a sodium salt of) L-012 were evaluated.

First, 1 mL of each of the reagents for measuring a luminescence, Solutions 1 (Solution 1-A, Solution 1-B, and Solution 1-C) obtained in (1) was transferred to two 5 mL test tubes. One of the test tubes was exposed to light from a fluorescent lamp at 430 to 450 Lx for 30 minutes (a reagent for measuring a luminescence with exposure, Solution 1), and the other was light-shielded by covering the test tube with aluminum foil (a reagent for measuring a luminescence with light shielding, Solution 1).

Subsequently, 10 to 50 μg of a reagent containing antigen-coupled magnetic particles (HBs antigen-coupled magnetic particle reagent), and 25 μL of a standard HBs antibody solution at an HBs antibody concentration of 250 mIU/mL, prepared with a 50 mM MOPS buffer solution (pH 7.5) containing 2% bovine serum albumin were added to and mixed in a test tube to perform a reaction at 37° C. for 3 minutes to form an "HBs antigen-coupled magnetic particle-HBs antibody" complex. After the reaction, the magnetic particles were collected by magnetism, using a neodymium magnet, the liquid was aspirated and removed by an aspirator, and then 100 μL of physiological saline was added thereto to disperse the magnetic particles, followed by collection by magnetism, and a washing operation for aspirating and removing the liquid by the aspirator was repeated three times.

Subsequently, 50 μL of the enzyme-labeled reagent (POD-labeled HBs antigen reagent) was added into the test tube to perform a reaction at 37° C. for 3 minutes to form an "HBs antigen-coupled magnetic particle-HBs antibody-POD-labeled HBs antigen" complex. After the reaction, the magnetic particles were collected by magnetism, using a neodymium magnet, the liquid was aspirated and removed by an aspirator, and then 100 μL of physiological saline was added thereto to disperse the magnetic particles, followed by collection by magnetism, and a washing operation for aspirating and removing the liquid by the aspirator was repeated twice.

Finally, 100 μL of each of the reagents for measuring a luminescence with exposure, Solutions 1 (Solution 1-A, Solution 1-B, and Solution 1-C) or the reagents for measuring a luminescence with light shielding, Solutions 1 (Solution 1-A, Solution 1-B, and Solution 1-C), and 100 μL of the reagent for measuring a luminescence, Solution 2, were simultaneously added thereto to perform a luminescent reaction at 37° C. for 43 seconds. Then, an average luminescence dose for 43 to 45 seconds after adding the reagents for measuring a luminescence, Solution 1 and Solution 2 simultaneously, was measured by a luminometer (Lumat LB9507: manufactured by Berthold Japan Co., Ltd.).

(6) Results

"The photostabilization effect of the stabilizers or the water-soluble dyes" and "the relative sensitivity with respect to luminol" were calculated from the obtained results, as shown below, and the various stabilizers or water-soluble dyes were evaluated. The results are each shown in Table 3.

<Photostabilization Effect of Stabilizers or Water-Soluble Dyes>

Regarding each of the reagents for measuring a luminescence, Solutions 1, a ratio of the average luminescence dose (luminescence dose with exposure) in the reagents for measuring a luminescence with exposure, Solutions 1 to the average luminescence dose (luminescence dose with light shielding) in the reagents for measuring a luminescence with light shielding, Solutions 1 [luminescence dose with exposure/luminescence dose with light shielding×100%=luminescence dose ratio] was calculated. The photostabilization effects of various stabilizers or water-soluble dyes were evaluated, based on the luminescence dose ratios.

That is, a luminescence dose ratio which is closer to 100% indicates that the photostabilization effects of various stabilizers or water-soluble dyes on (a sodium salt of) L-012 are high, and in view that the luminescence dose ratio was 67% in a case of using the reagent for measuring a luminescence, Solution 1-B, to which a stabilizer or water-soluble dye had not been added, the stabilizer or water-soluble dye contained in the reagent for measuring a luminescence, Solution 1-A, exhibiting a luminescence dose ratio of 72% or more, was evaluated to be a stabilizer or water-soluble dye which has a high photostabilization effect and can suppress a decrease in the measurement sensitivity during the exposure.

<Relative Sensitivity with Respect to Luminol>

Regarding each of the reagents for measuring a luminescence, Solution 1-A and Solution 1-B, a ratio of the luminescence dose with light shielding (L-012 luminescence dose) in each of the reagents for measuring a luminescence, Solution 1-A or Solution 1-B with respect to the luminescence dose with light shielding (luminol luminescence dose) in the reagent for measuring a luminescence, Solution 1-C [L-012 luminescence dose/luminol luminescence dose× 100%=relative sensitivity] was calculated. The measurement sensitivity of various stabilizers or water-soluble dyes was evaluated, based on the relative sensitivity.

That is, the reagent for measuring a luminescence, Solution 1-A, which exhibited a higher L-012 luminescence dose than the luminol luminescence dose (321,482 cps) was evaluated to be a reagent (L-012 luminescent reagent) having high measurement sensitivity and making it possible to perform measurements with higher sensitivity than that for the luminescence measurement using the luminol luminescence. In other words, the stabilizer or water-soluble dye contained in the reagent for measuring a luminescence, Solution 1-A, which exhibited a relative sensitivity of 100% or more, was evaluated to be a stabilizer or water-soluble dye which does not give an adverse effect on the luminescence intensity of L-012 and makes it possible to perform measurements with high sensitivity.

TABLE 3

| | | | | Luminescence dose (cps) | | | |
| --- | --- | --- | --- | --- | --- | --- | --- |
| Examples | Reagent | Stabilizer | Concentration | Luminescence dose with light shielding | Luminescence dose with exposure | Luminescence dose ratio (%) | Relative sensitivity (%) |
| Example 28 | Solution 1-A | Azomethine H | 0.05 μM | 634,920 | 526,277 | 83 | 197 |
| Example 29 | Solution 1-A | | 0.1 μM | 512,987 | 424,889 | 83 | 160 |
| Example 30 | Solution 1-A | New Coccine | 0.05 μM | 801,594 | 618,200 | 77 | 249 |
| Example 31 | Solution 1-A | | 0.1 μM | 855,859 | 623,586 | 73 | 266 |
| Example 32 | Solution 1-A | | 0.5 μM | 824,050 | 603,028 | 73 | 256 |
| Example 33 | Solution 1-A | | 1 μM | 822,063 | 599,850 | 73 | 256 |
| Example 34 | Solution 1-A | Sulfanilic acid | 1 μM | 826,752 | 647,482 | 78 | 257 |

TABLE 3-continued

| Examples | Reagent | Stabilizer | Concentration | Luminescence dose with light shielding | Luminescence dose with exposure | Luminescence dose ratio (%) | Relative sensitivity (%) |
|---|---|---|---|---|---|---|---|
| Example 35 | Solution 1-A | azochromtrop | 10 μM | 717,446 | 643,437 | 90 | 223 |
| Example 36 | Solution 1-A | Metanil Yellow | 1 μM | 826,491 | 606,059 | 73 | 257 |
| Example 37 | Solution 1-A | | 10 μM | 792,933 | 668,537 | 84 | 247 |
| Example 38 | Solution 1-A | Ponceau S | 1 μM | 833,179 | 686,334 | 82 | 259 |
| Example 39 | Solution 1-A | | 10 μM | 777,020 | 654,278 | 84 | 242 |
| Example 40 | Solution 1-A | | 100 μM | 570,843 | 485,055 | 85 | 178 |
| Example 41 | Solution 1-A | Tartrazine | 1 μM | 866,469 | 688,004 | 79 | 270 |
| Example 42 | Solution 1-A | | 10 μM | 840,689 | 694,914 | 83 | 262 |
| Example 43 | Solution 1-A | | 100 μM | 675,466 | 600,330 | 89 | 210 |
| Comparative Example 29 | Solution 1-B | — | — | 881,359 | 590,311 | 67 | 274 |
| Comparative Example 30 | Solution 1-C | — | — | 321,482 | 313,358 | 97 | — |

Azomethine H: 4-Hydroxy-5-(salicylidenamino)-2,7-naphthalenedisulfonic acid
New Coccine: 7-Hydroxy-8-(4-sulfo-1-naphthylazo)-1,3-naphthalenedisulfonic acid, trisodium salt
Sulfanilic acid azochromtrop: 2-(4-Sulfophenylazo)-1,8-dihydroxy-3,6-naphthalenedisulfonic acid, trisodium salt
Metanil Yellow: 3-[4-(Phenylamino)phenylazo]benzenesulfonic acid, sodium salt
Ponceau S: 3-Hydroxy-4-[4-(4-sulfophenylazo)-2-sulfophenylazo]-2,7-naphthalenedisulfonic acid, tetrasodium salt
Tartrazine: 4,5-Dihydro-5-oxo-1-(4-sulfophenyl)-4-[(4-sulfophenyl)azo]-1H-pyrazole-3-carboxylic acid, trisodium salt From the results in Table 3, it could be seen that any of Azomethine H, New Coccine, Sulfanilic acid azochromtrop, Metanil Yellow, Ponceau S, and Tartrazine, each of which is the stabilizer of the present invention, has both of an effect of suppressing a decrease in measurement sensitivity due to exposure (photostabilization effect) and an effect of making it possible to perform measurements with high sensitivity with little influence on the luminescence intensity of (a sodium salt of) L-012.

—Preparation of Reagent in Measurement System of Aldosterone Using Peroxidase (POD) and Measurement of Aldosterone—

Preparation of reagents, and measurements method and evaluation methods for aldosterone using various stabilizers or water-soluble dyes in a measurement system of an aldosterone using a peroxidase (POD) are set forth below.

Examples 45 to 48 and Comparative Examples 31 to 36

(1) Preparation of Reagents for Measuring Luminescence, Solutions 1

(a) Preparation of Reagent for Measuring Luminescence, Solution 1-A (Examples 45 to 48)

Into a 100 mL volumetric flask were introduced 15.6 mg of 8-amino-5-chloro-7-phenylpyrido[3,4-d]pyridazine-1,4(2H,3H)-dione, sodium salt (manufactured by Wako Pure Chemical Industries, Ltd.) and 3.5 mg of 4-(4-hydroxyphenyl)thiazole (manufactured by Wako Pure Chemical Industries, Ltd.). Subsequently, Azomethine H was added thereto in such an amount that the final concentration during the chemiluminescence measurement reached a predetermined concentration shown in Table 4. In addition, 20 mL of a 3-[4-(2-hydroxyethyl)-1-piperazinyl]propanesulfonic acid (EPPS)/sodium hydroxide buffer solution (250 mM, pH 8.0) was added thereto, then the volume of the solution was adjusted to 100 mL with distilled water, and the solution was uniformly mixed at 25° C. to prepare a reagent for measuring a luminescence, Solution 1-A, which was stored under refrigeration (2° C. to 10° C.) until use in the measurement.

(b) Preparation of Reagent for Measuring Luminescence, Solution 1-B (Comparative Examples 31 to 33)

Into a 100 mL volumetric flask were introduced 15.6 mg of 8-amino-5-chloro-7-phenylpyrido[3,4-d]pyridazine-1,4(2H,3H)-dione, sodium salt (manufactured by Wako Pure Chemical Industries, Ltd.) and 3.5 mg of 4-(4-hydroxyphenyl)thiazole (manufactured by Wako Pure Chemical Industries, Ltd.). Subsequently, 20 mL of a 3-[4-(2-hydroxyethyl)-1-piperazinyl]propanesulfonic acid (EPPS)/sodium hydroxide buffer solution (250 mM, pH 8.0) was added thereto, then the volume of the solution was adjusted to 100 mL with distilled water, and the solution was uniformly mixed at 25° C. to prepare a reagent for measuring a luminescence, Solution 1-B, which was stored under refrigeration (2° C. to 10° C.) until use in the measurement.

(c) Preparation of Reagent for Measuring Luminescence, Solution 1-C Comparative Examples 34 to 36)

Into a 100 mL volumetric flask were introduced 40 mg of luminol, sodium salt (manufactured by Wako Pure Chemical Industries, Ltd.) and 3.5 mg of 4-(4-hydroxyphenyl)thiazole (manufactured by Wako Pure Chemical Industries, Ltd.). Subsequently, 20 mL of a boric acid/sodium hydroxide buffer solution (250 mM, pH 8.55) was added thereto, then the volume of the solution was adjusted to 100 mL with distilled water, and the solution was uniformly mixed at 25° C. to prepare a reagent for measuring a luminescence, Solution 1-C, which was stored under refrigeration (2° C. to 10° C.) until use in the measurement.

(2) Preparation of Reagent Containing Magnetic Particles (Anti-Mouse IgG Polyclonal Antibody (Goat)-Coupled Magnetic Particle Reagent)

Into a lidded polyethylene bottle having 80 mL of a 97%-by-weight ethanol solution containing 3-aminopropyltriethoxysilane were added 20 mL of magnetic particles (prepared in accordance with Production Example 1 described in WO 2012/173002) to perform a reaction at 25°

C. for 1 hour. Then, the magnetic particles were collected by magnetism, using a neodymium magnet, and the liquid was aspirated and removed by an aspirator. Subsequently, 80 mL of a 10 mM acetate buffer solution (pH 5.1) was added thereto, the bottle was capped, and the polyethylene bottle was slowly inverted twice and stirred, and then the magnetic particles were collected by magnetism using a neodymium magnet. The liquid was aspirated and removed by an aspirator, and the magnetic particles were washed. This washing operation was repeated four times.

The magnetic particles after the washing were added into a lidded polyethylene bottle having 80 mL of a 0.5%-by-weight ethanol solution of succinic anhydride to perform a reaction at 25° C. for 2 hours. After the reaction, 80 mL of a 100 mM 2-(N-morpholino)ethanesulfonic acid (MES) buffer solution (pH 5.0) was added thereto, the bottle was capped, and the polyethylene bottle was slowly inverted twice and stirred, and then the magnetic particles were collected by magnetism using a neodymium magnet. The liquid was aspirated and removed by an aspirator, and the magnetic particles were washed. This washing operation was repeated four times.

In addition, the magnetic particles after the washing were added into a lidded polyethylene bottle having 80 mL of a 100 mM MES buffer solution (pH 5.0) containing an anti-mouse IgG polyclonal antibody (goat) (manufactured by Jackson ImmunoResearch Inc.) at a concentration of 100 µg/mL to perform a reaction at 25° C. for 15 to 25 hours. After the reaction, the magnetic particles were collected by magnetism, using a neodymium magnet, and washed with an MES buffer solution, and then 8 mL of a 0.03% aqueous glutaraldehyde solution was added thereto, and the mixture was reacted at 25° C. for 2 hours. Subsequently, 19.2 mg of sodium borohydride was added thereto, the mixture was reacted at 25° C. for 30 minutes, and then the magnetic particles were collected by magnetism, using a neodymium magnet, and washed with an MES buffer solution. Then, a blocking solution {50 mM MES buffer solution (pH 5.5) containing 0.5% of Block Ace (Manufactured by Snow Brand Milk Products Co., Ltd.)} was added thereto, and the mixture was reacted at 25° C. for 15 to 25 hours to prepare an anti-mouse IgG polyclonal antibody (goat)-coupled magnetic particles. In addition, the magnetic particles were collected by magnetism, using a neodymium magnet, and the blocking solution was aspirated and removed by an aspirator. Then, this was diluted with an MES buffer solution (pH 5.5) to a concentration of 0.5 mg/mL in terms of an anti-mouse IgG polyclonal antibody-coupled magnetic particle concentration to prepare a reagent containing antibody-coupled magnetic particles (anti-mouse IgG polyclonal antibody (goat)-coupled magnetic particle reagent), which was stored under refrigeration (2° C. to 10° C.) until use in the measurement.

(3) Preparation of Buffer Solution for Immune Reaction (Buffer Solution Containing Anti-Aldosterone Monoclonal Antibody (Mouse))

0.1 mL of an anti-aldosterone monoclonal antibody (mouse) (manufactured by ITM Co., Ltd.) was added to 100 mL of a 200 mM N-[tris(hydroxymethyl)methyl]glycine (Tricine) buffer solution (pH 8.2), and then the mixture was stirred at 25° C. for 5 minutes to prepare a 200 mM N-[tris(hydroxymethyl)methyl]glycine buffer solution (pH 8.2) containing an anti-aldosterone monoclonal antibody (mouse) at a concentration of 1 mL/L, thereby obtaining a buffer solution for an immune reaction, which was stored under refrigeration (2° C. to 10° C.) until use in the measurement.

(4) Preparation of Enzyme-Labeled Reagent (Peroxidase (POD)-Labeled Aldosterone Antigen Reagent)

A POD-labeled aldosterone antigen was prepared by the method described in literature (S. YOSHITAKE, M. IMAGAWA, E. ISHIKAWA, H. OGAWA; J Biochem (1982) Vol. 92, (5): 1413-1424), using an aldosterone antigen (manufactured by Sigma-Aldrich Corporation) and a horseradish-derived POD (manufactured by Roche Diagnostics K.K.). This was diluted with a 50 mM N-(2-acetamido)-2-aminoethanesulfonic acid (ACES) buffer solution (pH 7.2) to a concentration of 1.0 mL/L in terms of a POD-labeled aldosterone antigen concentration to prepare an enzyme-labeled reagent (POD-labeled aldosterone antigen reagent), which was stored under refrigeration (2° C. to 10° C.) until use in the measurement.

(5) Preparation of Reagent for Measuring Luminescence, Solution 2

Into a 100 mL volumetric flask was introduced 67 µL of aqueous hydrogen peroxide (manufactured by Wako Pure Chemical Industries, Ltd., special grade reagent, concentration of 30% by weight). Subsequently, the volume of the solution was adjusted to 100 mL with distilled water, and the solution was uniformly mixed at 25° C. to prepare a reagent for measuring a luminescence, Solution 2, which was stored under refrigeration (2° C. to 10° C.) until use in the measurement.

(6) Measurement of Chemiluminescence

A luminescence dose (average value) was measured, based on the reagents for measuring a luminescence, Solutions 1, according to Examples 45 to 48 and Comparative Examples 31 to 36 by the measurement method shown below, using each of the obtained reagents, and the photostabilization effect of Azomethine H, and the presence or absence of an effect on the luminescence intensity of (a sodium salt of) L-012 were evaluated.

First, 1 mL of each of Solution 1-A and Solution 1-B among the reagents for measuring a luminescence, Solutions 1, obtained in (1) was transferred to two 5 mL test tubes. One of the test tubes was exposed to light from a fluorescent lamp at 430 to 450 Lx for 30 minutes (a reagent for measuring a luminescence with exposure, Solution 1), and the other was light-shielded by covering the test tube with aluminum foil (a reagent for measuring a luminescence with light shielding, Solution 1). 1 mL of Solution 1-C was transferred to one 5 mL test tube, and the test tube was covered with aluminum foil to perform light shielding (reagent for measuring a luminescence with light shielding, Solution 1).

Subsequently, 10 to 50 µg of a reagent containing antibody-coupled magnetic particles (anti-mouse IgG polyclonal antibody (goat)-coupled magnetic particle reagent), 25 µL of a standard aldosterone solution at an aldosterone concentration of 0 to 800 pg/mL, prepared with a 15 mM phosphate buffer solution (pH 7.2) containing 1% bovine serum albumin, and 50 µL of a buffer solution for an immune reaction were added to and mixed in a test tube to perform a reaction at 37° C. for 3 minutes. In addition, 50 µL of the enzyme-labeled reagent (POD-labeled aldosterone antigen reagent) was added into the test tube and reacted at 37° C. for 3 minutes to form an "anti-mouse IgG polyclonal antibody (goat)-coupled magnetic particle-anti-aldosterone monoclonal antibody (mouse)-POD-labeled aldosterone antigen" complex. After the reaction, the magnetic particles were collected by magnetism, using a neodymium magnet, the liquid was aspirated and removed by an aspirator, and then 100 μL of physiological saline was added thereto to disperse the magnetic particles, followed by collection by magnetism, and a washing operation for aspirating and removing the liquid by the aspirator was repeated twice.

Finally, 100 μL of each of the reagents for measuring a luminescence with exposure, Solutions 1 (Solution 1-A and Solution 1-B) or the reagents for measuring a luminescence with light shielding, Solutions 1 (Solution 1-A, Solution 1-B, and Solution 1-C), and 100 μL of the reagent for measuring a luminescence, Solution 2, were simultaneously added thereto, the luminescent reaction was performed at 37° C. for 43 seconds. Then, an average luminescence dose for 43 to 45 seconds, after adding the reagents for measuring a luminescence, Solution 1 and Solution 2 simultaneously, was measured by a luminometer (Lumat LB9507: manufactured by Berthold Japan Co., Ltd.).

(7) Results

"The photostabilization effect of Azomethine H (stabilizer)" and "the relative sensitivity with respect to luminol" were calculated from the obtained results, as shown below, and Azomethine H (stabilizer) was evaluated. The results are each shown in Table 4.

nescence dose ratio] was calculated. The photostabilization effect of Azomethine H (stabilizer) was evaluated, based on the luminescence dose ratios.

That is, a luminescence dose ratio which is closer to 100% indicates that the photostabilization effect of Azomethine H (stabilizer) on (a sodium salt of) L-012 is high, and it was examined whether a higher luminescence dose ratio than the luminescence dose ratio in a case of using the reagent for measuring a luminescence, Solution 1-B, to which Azomethine H (stabilizer) had not been added was exhibited or not at the respective aldosterone concentrations shown in Table 4, and thus, the relationship between the concentration range of aldosterone and the photostabilization effect was evaluated.

<Relative Sensitivity with Respect to Luminol>

Regarding each of the reagents for measuring a luminescence, Solution 1-A and Solution 1-B, a ratio of the luminescence dose with light shielding (L-012 luminescence dose) in each of the reagents for measuring a luminescence, Solution 1-A or Solution 1-B with respect to the luminescence dose with light shielding (luminol luminescence dose) in the reagent for measuring a luminescence, Solution 1-C [L-012 luminescence dose/luminol luminescence dose× 100%=relative sensitivity] was calculated. The measurement sensitivity of Azomethine H (stabilizer) was evaluated, based on the relative sensitivity.

That is, it was examined whether a higher L-012 luminescence dose than the luminol luminescence dose was exhibited or not at the respective aldosterone concentrations shown in Table 4, and thus, the relationship between the concentration range of aldosterone and the measurement sensitivity was evaluated.

TABLE 4

| Examples | Reagent | ALD standard solution | Stabilizer | Concentration | Luminescence dose (cps) | | Luminescence dose ratio (%) | Relative sensitivity (%) |
|---|---|---|---|---|---|---|---|---|
| | | | | | Luminescence dose with light shielding | Luminescence dose with exposure | | |
| Example 44 | Solution 1-A | 0 pg/mL | Azomethine H | 0.1 μM | 1,652,310 | 1,407,817 | 85 | 337 |
| Example 45 | Solution 1-A | | | 0.5 μM | 503,287 | 575,777 | 114 | 103 |
| Example 46 | Solution 1-A | 100 pg/mL | | 0.1 μM | 1,137,125 | 1,227,820 | 108 | 286 |
| Example 47 | Solution 1-A | 800 pg/mL | | 0.1 μM | 140,838 | 165,479 | 117 | 168 |
| Comparative Example 31 | Solution 1-B | 0 pg/mL | — | — | 2,834,737 | 1,841,217 | 65 | 578 |
| Comparative Example 32 | Solution 1-B | 100 pg/mL | — | — | 2,246,053 | 1,438,727 | 64 | 565 |
| Comparative Example 33 | Solution 1-B | 800 pg/mL | — | — | 454,355 | 223,750 | 49 | 542 |
| Comparative Example 34 | Solution 1-C | 0 pg/mL | — | — | 490,198 | — | — | — |
| Comparative Example 35 | Solution 1-C | 100 pg/mL | — | — | 397,365 | — | — | — |
| Comparative Example 36 | Solution 1-C | 800 pg/mL | — | — | 83,790 | — | — | — |

ALD: Aldosterone
Azomethine H: 4-Hydroxy-5-(salicylidenamino)-2,7-naphthalenedisulfonic acid <Photostabilization Effect of Azomethine H (Stabilizer)>

Regarding each of the reagents for measuring a luminescence, Solutions 1, a ratio of the average luminescence dose (luminescence dose with exposure) in the reagents for measuring a luminescence with exposure, Solutions 1 to the average luminescence dose (luminescence dose with light shielding) in the reagents for measuring a luminescence with light shielding, Solutions 1 [luminescence dose with exposure/luminescence dose with light shielding×100%=lumi- From the results in Table 4, it could be seen that Azomethine H, which is the stabilizer of the present invention, has both of an effect of suppressing a decrease in measurement sensitivity due to exposure (photostabilization effect) and an effect of making it possible to perform measurements with high sensitivity with little influence on the luminescence intensity of (a sodium salt of) L-012 in a wide concentration range in which the concentration of aldosterone is 0 to 800 pg/mL, and therefore, the stabilizer of the present invention has both of the photostabilization effect and an effect of making it possible to perform measurements with high sensitivity, irrespective of the concentrations of target materials (subjects for measurement).

From the results in Tables 1 to 4, it could be seen that even in a case where any one of Azomethine H, New Coccine, Sulfanilic acid azochromtrop, Metanil Yellow, Ponceau S, and Tartrazine, each of which is the stabilizer of the present invention, was used as a stabilizer for L-012 or a salt thereof, a higher luminescence dose ratio than that in a case of not using a stabilizer is exhibited, and therefore, the stabilizer of the present invention suppresses deterioration (decomposition) of L-012 or a salt thereof due to exposure (has the photostabilization effect). Therefore, in a case where the stabilizer of the present invention is coexisted with a measurement solution (luminescent substrate solution) containing L-012 or a salt thereof in the chemiluminescence measurement, the stabilizer can suppress a decrease in measurement sensitivity due to exposure, and as a result, it is not necessary to perform light shielding for a measurement solution (luminescent substrate solution) containing L-012 or a salt thereof. Therefore, the stabilizer can be more simply provided for measurements. In addition, it could be seen that the stabilizer of the present invention hardly gives an adverse effect on the luminescence dose of L-012 or a salt thereof itself, and allows measurements with higher sensitivity, as compared with luminescence measurements using luminol luminescence. Therefore, in a case where the stabilizer of the present invention is coexisted with a measurement solution (luminescent substrate solution) containing L-012 or a salt thereof in the chemiluminescence measurement, it does not give an adverse effect on the measurements, and target materials (subjects for measurement) can be measured with high sensitivity and high accuracy. In addition, it could be seen that Azomethine H and New Coccine among these stabilizers typically have a high photostabilization effect, and target materials (subjects for measurement) can be measured with high sensitivity and high accuracy, irrespective of measurement systems. On the other hand, it could be seen that a photostabilization effect cannot be obtained or an adverse effect is given on measurements with water-soluble dyes such as N-Benzoyl H acid, monopotassium, monosodium salt, Alizarin Yellow GG, and Cresol Red, and thus, target materials (subjects for measurement) cannot be measured with high accuracy. It is suggested that the effects as described above have a relationship with the structures of stabilizers, considering that the effects have no relationship with the maximum absorption wavelength of the stabilizers.

From the above description, it could be seen that only the stabilizer of the present invention has both of an effect of stabilizing L-012 or a salt thereof and an effect of not giving an adverse effect on measurements. Therefore, it could be seen that in a case where the stabilizer of the present invention is coexisted with measurement solution (luminescent substrate solution) containing L-012 or a salt thereof in the chemiluminescence measurement, various target materials (subjects for measurement) in vivo can be measured with high sensitivity and high accuracy, and in a simple manner.

INDUSTRIAL APPLICABILITY

The stabilizer represented by the general formula [1] of the present invention is a compound which can suppress the decomposition (deterioration) of L-012 or a salt thereof which is a chemiluminescent material, due to exposure. In chemiluminescence measurements, it is possible to suppress the decomposition (deterioration) of L-012 or a salt thereof due to exposure by coexisting with the stabilizer of the present invention and L-012 or a salt thereof to stabilize L-012 or a salt thereof for a long period of time, and further, to suppress a reduction in the luminescence intensity (a decrease in the measurement sensitivity) of L-012 or a salt thereof.

In addition, the composition of the present invention and the kit for measuring a luminescence of the present invention contain L-012 or a salt thereof, and the compound represented by the general formula [1] (the stabilizer of the present invention), suppresses a reduction in the luminescence intensity (a decrease in the measurement sensitivity) of L-012 or a salt thereof due to exposure in a process for producing the composition or the kit, or during the use (measurement) of the composition or the kit, and hardly gives an adverse effect on the luminescence dose of L-012 or a salt thereof itself. Therefore, in a case where the composition or the kit is used in the chemiluminescence measurement, for example, a target material (subject for measurement) in vivo can be measured with high sensitivity and high accuracy, and in a simple manner.

The invention claimed is:

1. A stabilization method for 8-amino-5-chloro-7-phenylpyrido[3,4-d]pyridazine-1,4(2H,3H)-dione or a salt thereof, wherein a compound selected from 4-hydroxy-5-(salicylidenamino)-2,7-naphthalenedisulfonic acid or a salt thereof, 7-hydroxy-8-(4-sulfo-1-naphthylazo)-1,3-naphthalenedisulfonic acid or a salt thereof, 2-(4-sulfophenylazo)-1,8-dihydroxy-3,6-naphthalenedisulfonic acid or a salt thereof, 3-[4-(phenylamino)phenylazo]benzenesulfonic acid or a salt thereof, and 3-hydroxy-4-[4-(4-sulfophenylazo)-2-sulfophenylazo]-2,7-naphthalenedisulfonic acid or a salt thereof is coexisted with 8-amino-5-chloro-7-phenylpyrido[3,4-d]pyridazine-1,4(2H,3H)-dione or a salt thereof.

2. The stabilization method according to claim 1, wherein the compound is 4-hydroxy-5-(salicylidenamino)-2,7-naphthalenedisulfonic acid or a salt thereof.

3. The stabilization method according to claim 1, wherein the compound is 7-hydroxy-8-(4-sulfo-1-naphthylazo)-1,3-naphthalenedisulfonic acid or a salt thereof.

4. The stabilization method according to claim 1, wherein the compound is 2-(4-sulfophenylazo)-1,8-dihydroxy-3,6-naphthalenedisulfonic acid or a salt thereof.

5. The stabilization method according to claim 1, wherein the compound is 3-[4-(phenylamino)phenylazo]benzenesulfonic acid or a salt thereof.

6. The stabilization method according to claim 1, wherein the compound is 3-hydroxy-4-[4-(4-sulfophenylazo)-2-sulfophenylazo]-2,7-naphthalenedisulfonic acid or a salt thereof.

7. A composition comprising 8-amino-5-chloro-7-phenylpyrido[3,4-d]pyridazine-1,4(2H,3H)-dione or a salt thereof, and a compound selected from 4-hydroxy-5-(salicylidenamino)-2,7-naphthalenedisulfonic acid or a salt thereof, 7-hydroxy-8-(4-sulfo-1-naphthylazo)-1,3-naphthalenedisulfonic acid or a salt thereof, 2-(4-sulfophenylazo)-1,8-dihydroxy-3,6-naphthalenedisulfonic acid or a salt thereof, 3-[4-(phenylamino)phenylazo]benzenesulfonic acid or a salt thereof, and 3-hydroxy-4-[4-(4-sulfophenylazo)-2-sulfophenylazo]-2,7-naphthalenedisulfonic acid or a salt thereof.

8. The composition according to claim 7, wherein the compound is 4-hydroxy-5-(salicylidenamino)-2,7-naphthalenedisulfonic acid or a salt thereof.

9. The composition according to claim 7, wherein the compound is 7-hydroxy-8-(4-sulfo-1-naphthylazo)-1,3-naphthalenedisulfonic acid or a salt thereof.

10. The composition according to claim 7, wherein the compound is 2-(4-sulfophenylazo)-1,8-dihydroxy-3,6-naphthalenedisulfonic acid or a salt thereof.

11. The composition according to claim 7, wherein the compound is 3-[4-(phenylamino)phenylazo]benzenesulfonic acid or a salt thereof.

12. The composition according to claim 7, wherein the compound is 3-hydroxy-4-[4-(4-sulfophenylazo)-2-sulfophenylazo]-2,7-naphthalenedisulfonic acid or a salt thereof.

13. A kit for measuring a luminescence, comprising 8-amino-5-chloro-7-phenylpyrido[3,4-d]pyridazine-1,3(2H, 3H)-dione or a salt thereof, and a compound selected from 4-hydroxy-5-(salicylidenamino)-2,7-naphthalenedisulfonic acid or a salt thereof, 7-hydroxy-8-(4-sulfo-1-naphthyl azo)-1,3-naphthalenedisulfonic acid or a salt thereof, 2-(4-sulfophenylazo)-1,8-dihydroxy-3,6-naphthalenedisulfonic acid or a salt thereof, 3-[4-(phenylamino)phenylazo]benzenesulfonic acid or a salt thereof, and 3-hydroxy-4-[4-(4-sulfophenylazo)-2-sulfophenylazo]-2,7-naphthalenedisulfonic acid or a salt thereof.

14. The kit for measuring a luminescence according to claim 13, wherein the compound is 4-hydroxy-5-(salicylidenamino)-2,7-naphthalenedisulfonic acid or a salt thereof.

15. The kit for measuring a luminescence according to claim 13, wherein the compound is 7-hydroxy-8-(4-sulfo-1-naphthylazo)-1,3-naphthalenedisulfonic acid or a salt thereof.

16. The kit for measuring a luminescence according to claim 13, wherein the compound is 2-(4-sulfophenylazo)-1, 8-dihydroxy-3,6-naphthalenedisulfonic acid or a salt thereof.

17. The kit for measuring a luminescence according to claim 13, wherein the compound is 3-[4-(phenylamino) phenylazo]benzenesulfonic acid or a salt thereof.

18. The kit for measuring a luminescence according to claim 13, wherein the compound is 3-hydroxy-4-[4-(4-sulfophenylazo)-2-sulfophenylazo]-2,7-naphthalenedisulfonic acid or a salt thereof.

* * * * *

UNITED STATES PATENT AND TRADEMARK OFFICE
CERTIFICATE OF CORRECTION

PATENT NO. : 10,961,185 B2
APPLICATION NO. : 15/770145
DATED : March 30, 2021
INVENTOR(S) : Shinya Kaji Page 1 of 1

It is certified that error appears in the above-identified patent and that said Letters Patent is hereby corrected as shown below:

On the Title Page

Column 1, at Item (73) Assignee:
"FUJIFILM WAKO PURE CHEMICAL CHEMICAL CORPORATION" should read "FUJIFILM WAKO PURE CHEMICAL CORPORATION"

Signed and Sealed this
Eighth Day of March, 2022

Drew Hirshfeld
*Performing the Functions and Duties of the*
*Under Secretary of Commerce for Intellectual Property and*
*Director of the United States Patent and Trademark Office*